United States Patent [19]
Vasilevskis et al.

[11] Patent Number: 4,720,474
[45] Date of Patent: Jan. 19, 1988

[54] OLEFIN OXIDATION CATALYST SYSTEM

[75] Inventors: Janis Vasilevskis, Los Gatos; Jacques C. De Deken, Palo Alto; Robert J. Saxton, Mountain View; Paul R. Wentrcek, Redwood City; Jere D. Fellmann, Livermore; Lyubov S. Kipnis, Sunnyvale, all of Calif.

[73] Assignee: Catalytica Associates, Mountain View, Calif.

[21] Appl. No.: 779,501

[22] Filed: Sep. 24, 1985

[51] Int. Cl.⁴ .............................................. B01J 31/02
[52] U.S. Cl. ................................... 502/165; 502/167; 502/170; 502/201; 502/204; 502/206; 502/207; 502/209; 502/210; 502/211; 502/213; 502/215; 502/217; 502/218; 502/219; 502/220; 502/221; 502/228; 502/230; 502/241; 502/242; 502/245; 502/254; 502/255; 502/262; 502/305; 502/308; 502/313; 502/314; 502/316; 502/324; 502/326; 502/331; 502/338; 502/339
[58] Field of Search .............. 502/165, 167, 170, 201, 502/204, 206, 207, 209, 210, 211, 213, 215, 217, 218, 219, 220, 221, 228, 230, 241, 242, 245, 254, 255, 262, 305, 308, 313, 314, 316, 324, 326, 331, 338, 339

[56] References Cited

U.S. PATENT DOCUMENTS

| | | | |
|---|---|---|---|
| 3,215,743 | 11/1965 | Riemenscheider et al. | 260/597 |
| 3,365,499 | 1/1968 | Clement et al. | 260/597 |
| 3,379,651 | 4/1968 | Hargis et al. | 502/211 |
| 4,042,623 | 8/1977 | Ogawa et al. | 502/213 X |
| 4,043,934 | 8/1977 | Shuler | 502/1 |
| 4,049,574 | 9/1977 | Kerr et al. | 502/209 |
| 4,152,354 | 5/1979 | Stapp | 260/597 B |
| 4,203,927 | 5/1980 | Stapp | 502/207 X |
| 4,386,217 | 5/1983 | Ainbinder et al. | 502/169 X |
| 4,400,544 | 8/1983 | Takehira et al. | 568/360 |
| 4,419,525 | 12/1983 | Shioyama et al. | 568/401 |
| 4,434,082 | 2/1984 | Murtha et al. | 502/164 |
| 4,447,638 | 5/1984 | Gaffney et al. | 502/209 |
| 4,447,639 | 5/1984 | Sofranko et al. | 502/209 X |
| 4,448,892 | 5/1984 | Kukes et al. | 502/167 X |
| 4,451,666 | 5/1984 | Sofranko et al. | 502/170 X |
| 4,473,705 | 9/1984 | Miyamori et al. | 502/210 X |
| 4,507,506 | 3/1985 | Shioyama | 568/401 |
| 4,507,507 | 3/1985 | Murtha | 586/401 |
| 4,568,770 | 2/1986 | Alper et al. | 568/401 |

FOREIGN PATENT DOCUMENTS

| | | |
|---|---|---|
| 828603 | 10/1975 | Belgium . |
| 0101223A2 | 2/1984 | European Pat. Off. . |
| 1359141 | 3/1964 | France . |
| 54-57488 | 11/1979 | Japan . |
| 56-138159 | 10/1981 | Japan . |
| 59-80619 | 5/1984 | Japan . |
| 1024684 | 5/1966 | United Kingdom . |
| 1259145 | 1/1972 | United Kingdom . |
| 1508331 | 4/1978 | United Kingdom . |
| 504754 | 2/1976 | U.S.S.R. . |

OTHER PUBLICATIONS

K. I. Matveev et al., "Kinetics of Oxidation of Ethylene to Acetaldyde by Phosphomolybdovanadic Heteropolyacids in the Presence of a Pd(II) Aquo Complex", Kinetika i Kataliz, vol. 18, pp. 320, Mar.–Apr. 1977.

K. Urabe et al., "Liquid Phase Oxidation of 1-Butene by Pd(II)–Heteropoly Acid", VII Int. Cong. on Catalysis, Tokyo (1980), 1418.

(List continued on next page.)

[57] ABSTRACT

The addition of redox-active metal components and ligands, alternatively or simultaneously, results in increased conversion and selectivity in the palladium-catalyzed oxidation of olefins to carbonyl products in the presence of polyoxoanions. In preferred modes, heteropolyoxoanions and isopolyoxoanions containing tungsten, molybdenum and vanadium, individually or in combination, are described. The use of copper as the redox-active metal component shows reduced allylic reactivity. The elimination of chloride from the catalyst system provides substantial engineering advantages over the prior art, particularly, the reduction of corrosion and chloro-organic by-product formation. The use of redox-active metal components and/or ligands makes the palladium-polyoxoanion catalyst system industrially practicable.

55 Claims, 2 Drawing Figures

OTHER PUBLICATIONS

Ogawa et al., "Liquid Phase Oxidation of Cyclo-olefins by a PdSO$_4$-Heteropolyacid Catalyst System", J.C.S. Chem Comm., pp. 1274-1275, (1981).

Ogawa et al., "Palladium(II) Sulfate-Heterpoly Acid--Catalyzed Oxidation of Cycloolefins", Bull, Chem. Soc. Jpn., vol. 57, pp. 1908-1913 (1984).

S. F. Davison et al., "Phosphomolybdic Acid as a Reoxidant in the Palladium(II)-Catalyzed Oxidation of But-1-ene to Butan-2-one", J.C.S. Dalton Trans., pp. 1223-1228 (1984).

K. Junuszkiewicz et al., "Palladium and Phase Transfer Catalyzed Oxidation of Olefins to Ketones, Sensitivity of the Reaction to the Nature of the Phase Transfer Agent", Tetrahedron Letters, vol. 24, No. 47, pp. 5159-5162 (1983).

J. S. Coe et al., "Kinetic Studies on Homogeneous Oxidation of Olefins with Palladium(II) Catalysts", J.C.S. Dalton, pp. 645-649 (1975).

K. I. Matveev, "Development of New Homogeneous Catalysts for the Oxidation of Ethylene to Acetaldehyde", Kinetika i Kataliz, vol. 18, No. 4, pp. 862-877 (1977).

Y. Izumi et al., "The Carbon-Supported Palladium-Vanadyl Sulfate-Sulfuric Acid Catalyst System for Heterogeneous Wacker Reactions", J. Catal., vol. 85, pp. 284-286 (1984).

A. M. Gaffney et al., "Heterogeneous Catalyst for Alcohol Oxycarbonylation to Dialkyl Oxalates", J. Catal., vol. 90, pp. 261-269 (1984).

A. B. Evnin et al., "Heterogeneously Catalized Vapor--Phase Oxidation of Ethylene to Acetaldehyde", Journal of Catalysis, 30, pp. 109-117 (1973).

P. M. Maitlis, "The Organic Chemistry of Palladium, vol. II Catalytic Reactions", Academic Press, New York, pp. 93-108, 1971.

I. V. Kozhevnikov et al., "Acetoxylation of Olefins Catalyzed by a Palladium(II)-Heteropolyacid System", Reaction Kinetics and Catalysis Letters, vol. 7, No. 3, pp. 297-302 (1977).

L. N. Pachkovskaya et al., "Ring Acetoxylation of Aromatic Compounds in the Presence of Palladium Complexes and Heteropoly Acids", Kinetika i Kataliz, vol. 18, No. 4, pp. 1040-1042, Aug. 1977.

A. I. Rudenkov et al., "Development of New Homogeneous Catalysis for the Oxidative Coupling of Aromatic Compounds", Kinetika i Kataliz, vol. 18, No. 4, pp. 915-920, Jul.-Aug., 1977.

I. V. Kozhevnikov et al., "Kinetics and Mechanism of the Oxidation of Isopropanol in the Presence of the System Pd(II)-Heteropolyacid", Kinetika i Kataliz, vol. 21, No. 4, pp. 947-953, Jul.-Aug. 1980.

*The Condensed Chemical Dictionary*, Ninth Edition, (1977), Pub. by V. N. Reinhold Co., N.Y., N.Y., p. 512.

J. Am. Chem. Soc., 1981, 103, pp. 7831-7383.

J. Am. Chem. Soc., 1980, 102, pp. 6864-6866.

J. Am. Chem. Soc., 1983, 105, pp. 4286-4292.

Prepera et al., J. Am. Chem. Soc., 1985, 107, pp. 4883-4892.

Reactivity of Solids, vol. 2, Material Monograph 10, Dyrek, K. et al., Editors (1982)—See Article p. 685 by Poli, including Figures.

Centi, G. et al., *Appld. Catal.* 1984, 9, 177-190.

Hodnett, B. K., Catal. Rv. Sci., Eng., 1985, 27, 373-424.

Pope, M. T., in "Heteropoly and Isopoly Oxometallates"; Springer-Verlag, New York, 1983, pp. 7-14.

O'Donnell, S. E.; Pope, M. T.; *J.C.S. Dalton*, 1976, pp. 2290-2297.

Davison, S. F.; Mann, B. E.; Maitlis, P. M.; *J.C.S. Dalton*, 1984, pp. 1223-1228.

Maksimovaskaya, R. I.; Fedotov, M. A.; *Russ. J. Inorg. Chem.*, 1985, 30, pp. 57-61.

Il'yasova, A. K.; Akkmetova, A. K.; *Russ. J. Inorg. Chem.*, 1985, 30, pp. 368-372.

Gatehouse, B. M., Jozsa, A. J.; *J.C.S. Chem. Comm.*, 1977, pp. 674-675.

Alzadeh, M. H.; Harmalker, S. P.; Jeannin, Y.; Martin-Frere, J.; Pope, M. T.; *J. Am. Chem. Soc.*, 1985, 107, pp. 2662-2669.

Kepert, D. L.; Kyle, J. H.; *J.C.S. Dalton*, 1978, pp. 137-141.

Kepert, D. L.; Kyle, J. H.; *J.C.S. Dalton*, 1978, pp. 1781-1784.

Finke, R. G.; Rapko, B.; Saxton, R. J.; Domaille, P. J.; *J. Am. Chem. Soc.*, 1986, 108, pp. 2947-2960.

Highfield, J. G.; Moffatt, J. B.; *J. Catal.*, 1984, 88, pp. 177-187.

Akimoto, J.; Tsuchida, Y.; Sato, K.; Echigoya, G.; *J. Catal.*, 1981, 72, pp. 83-94.

Koniski, Y.; Sakata, K.; Misono, M.; Yoneda, Y.; *J. Catal.*, 1982, 77, pp. 169-179.

Misono, M.; Mizumo, N.; Katamura, K.; Kasai, A.; Koniski, Y.; Sakata, K.; Okyhara, T.; Yoneda Y.; Bull. Chem. Soc. Jpn., 1982, 55, pp. 400-406.

Hodnett, B. K.; Moffatt, J. B.; *J. Catal.*, 1984, 88, pp. 253-263.

Domaille, P. J., *Inorg. Chem.*, 1986, 25, pp. 1239-1242.

*Primary Examiner*—Patrick P. Garvin
*Attorney, Agent, or Firm*—Limbach, Limbach & Sutton

VARIATION OF CORROSION RATE OF SS 316 WITH CHLORIDE CONCENTRATION

OLEFIN OXIDATION CATALYST SYSTEM

DESCRIPTION

TECHNICAL FIELD

This invention relates generally to palladium catalyzed oxidation of olefins to carbonyl compounds. More specifically, this invention relates to the use of heteropolyoxoanions and isopolyoxoanions in a one stage liquid phase oxidation of olefins with molecular oxygen. The addition of redox active metals and ligands, alternatively or simultaneously, to the catalyst system improves conversion and selectivity to the desired carbonyl products.

BACKGROUND OF THE INVENTION

The catalyst compounds and systems of the present invention are useful in the production of ketones which are important industrial commodity chemicals. For example, methyl ethyl ketone and methyl isobutyl ketone find use as solvents. Further the present invention can be used to make heretofore unavailable ketones which can serve as new classes of useful specialty chemical products, or intermediates used in their production.

Palladium catalysts are useful in the oxidation of unsaturated hydrocarbons. One large class of hydrocarbons is olefins. Depending on the catalyst composition and reaction conditions, a number of different major reaction products may result. The generalized examples are:

(1) allylic oxidation

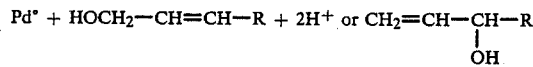

(2) diol formation

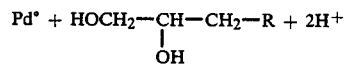

(3) Wacker oxidation to carbonyl product

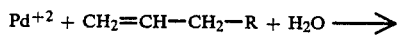

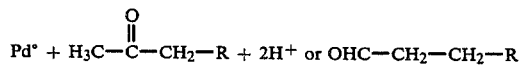

(4) Reaction with a general nucleophile (Nu$^-$)

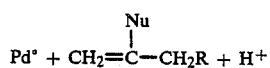

A good summary of palladium catalyzed olefin oxidations can be found in Chapter 7 of "Metal-Catalyzed Oxidations of Organic Compounds" by Sheldon and Kochi (Academic Press, N.Y., 1981). A more specific review, "Synthetic Applications of the Palladium Catalyzed Oxidation of Olefins to Ketones" has been written by J. Tsuji; Synthesis 5, 369-384 (1984).

In the oxidations outlined above, $Pd^{+2}$ is reduced. The overall reactions can be made catalytic if the palladium can be reoxidized by an oxidizing agent. Preferentially, one would use plentiful and cheap oxygen from air. The direct reoxidation of palladium by oxygen is thermodynamically possible but kinetically too slow. As a result, a co-catalyst is required to speed up the overall oxidation process.

The Wacker-type oxidation process of the prior art uses $PdCl_2/CuCl_2$ as the catalyst system where $Cu^{+2}$ plays the role of the co-catalyst.

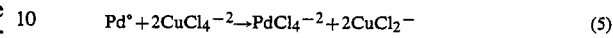 (5)

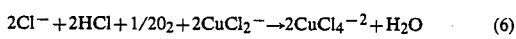 (6)

It should be noted that the copper is necessary to improve palladium reoxidation kinetics. Chloride ($Cl^-$) is an essential ingredient since as a $Pd^{+2}$ ligand, it provides a driving force for reaction (5) and, as a $Cu^{+2}$ ligand, it makes reaction (6) possible.

The above Wacker system, however, presents several substantial engineering problems making commercial application difficult. The use of chlorides results in severe corrosion, requiring the use of expensive, i.e. titanium-clad, reactor vessels. Further, the presence of chloride ions results in the formation of undesirable chlorinated byproducts which lowers the overall yield of desired material. In addition, these chlorinated byproducts often prove difficult to separate from the desired product.

In response to these unfavorable characteristics of Wacker-type catalysts, new systems have been developed by others to reduce the level of chloride present in the olefin oxidation system. The best examples of these newly developed systems can be found in Belgian Pat. No. 828,603, the work of Ogawa et al., J.C.S. Chem. Comm, 1274-75 (1981), and U.S. Pat. No. 4,434,082.

Belgian Pat. No. 828,603 (Oct. 30, 1975) teaches the use of polyoxoanions as co-catalysts to regenerate $Pd^{+2}$. The reduced polyoxoanions are subsequently reoxidized with oxygen. Such polyoxoanions can be generally described in the following way.

In aqueous solution certain metal oxides undergo stepwise hydrolysis-oligomerization reactions upon acidification according to the following representative stoichiometries ["Heteropoly and Isopoly Oxometalates" by M. T. Pope (Springer-Verlag, N.Y., 1983)]:

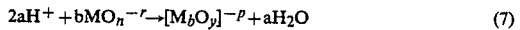 (7)

where
bn=y+a (oxygen atom balance)
br−2a=p (charge balance)

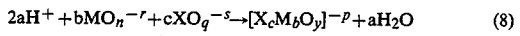 (8)

where
bn+cq=y+a (oxygen atom balance)
br+cs−2a=p (charge balance)

and where M can be one of several metals, e.g. W, Mo, V, or mixtures of these metals. X is usually P or Si but can be a number of other elements. The condensed metal oxides, e.g. $[X_cM_bO_y]^{-p}$, form a symmetric three dimensional array whose structure and composition can vary a great deal with various X's and M's. Which structure is present depends on the acidity of the solution, the initial amounts of $MO_n^{-r}$ and $XO_q^{-s}$, and other reaction conditions. In some cases, even under the same reaction conditions, different structures may be present. Products formed by reaction (7) are called isopolyoxoanions. Products formed by reaction (8) contain a "hetero" atom X, usually centrally located in the structure, and as a result these products are referred to as heteropolyoxoanions. Hereinafter, polyoxoanion (POA) may be used to refer to heteropolyoxoanions and isopolyoxoanions. Those skilled in the art would be capable of differentiating heteropolyoxoanions from isopolyoxoanions when necessary for clarity.

The Belgian patent discloses a number of heteropolyoxoanion compositions, mostly containing mixtures of molybdenum and vanadium, useful in the oxidation of ethylene to acetaldehyde, propylene to acetone, butene to methyl ethyl ketone and 1-hexene to 2-hexanone. It is also disclosed that isopolyoxoanion compositions can lead to unstable catalyst systems. Further, it is disclosed that an increase in the number of vanadium atoms from one to six is observed to cause an increase in the beneficial characteristics of the catalyst, which catalyst can be prepared in situ without isolation.

High selectivity is predicted for a large number of olefins but only shown for $C_2$ to $C_4$ in which cases isomerization either cannot occur ($C_2$), occurs to give the same structure ($C_3$), or occurs to give different isomers which react to the same product ($C_4$) as shown in equation (9).

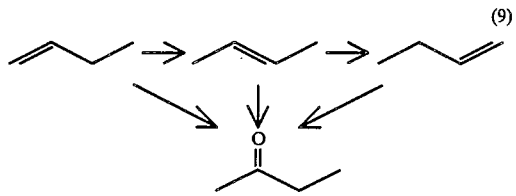

(9)

The examples disclosed in the Belgian patent show that when 1-hexene is used, selectivity to 2-hexanone drops significantly due to isomerization.

The iso- and heteropolyoxoanions of the instant invention, e.g. $PMo_6V_6O_{40}^{-9}$, $PW_6Mo_6O_{40}^{-3}$, $P_2W_{15}V_3O_{62}^{-9}$, are used in conjunction with a redox active metal and (or) a ligand for the redox active metal and (or) the palladium component. The addition of the redox active metal component and the ligand, either singly or in combination, results in greatly improved conversions and selectivities not taught by the prior art.

The Belgian patent teaches the use of the polyoxoanion component and the palladium component in ratios of 100:1–1000:1, which leads to very high POA loadings. Lower ratios (2:1 and 33.3:1) require high palladium concentrations. The instant invention reduces the amount of isopolyoxoanion or heteropolyoxoanion required such that favorable catalyst activity is observed when polyoxoanion:Pd ratios of 0.5:1–10:1 are used. The disparity in co-catalyst (POA) loading between the Belgian patent and the instant invention is partially attributable to the fact that the overall oxidation process disclosed in the Belgian patent requires two stages.

In the first stage of that process, the palladium component oxidizes the olefin. In order to achieve commercially acceptable turnovers of the olefin on palladium, large molar amounts of polyoxoanions are required. This results from the fact that the reaction is stoichiometric in the polyoxoanion due to the absence of molecular oxygen. As a result of the high molecular weight of these compounds, large masses of these compounds are correspondingly loaded, rendering commercial operation impractical from solubility, viscosity and catalyst distribution standpoints. Once all the polyoxoanion is reduced, the palladium can precipitate out as the metal (zero valent state). In the second stage, after removal of hydrocarbons, oxygen is added to reoxidize the polyoxoanion.

The favorable catalyst activity of the instant invention enables a one stage oxidation process. While a proper choice of the hydrocarbon/oxidant feed composition and proper reactor design can eliminate potential safety hazards, a one-stage process not only eliminates the need for a second stage, but also eliminates the engineering problems associated with the handling of high viscosity fluids resulting from the use of high polyoxoanion concentrations. The addition of a redox active metal and (or) ligand for the palladium and (or) the redox active metal, not only further reduces the amount of heteropolyoxoanion needed, but in a number of cases these additives produce active polyoxoanion systems from otherwise inactive ones, e.g., $P_2W_{12}Mo_6O_{62}^{-6}$, which by itself does not reoxidize with oxygen. In addition, the presence of a redox active metal and (or) ligand, unexpectedly increases the olefin oxidation rate and also improves the selectivity and yield to the desired carbonyl product. Furthermore, by using less polyoxoanion, the cost of the catalyst per unit of hydrocarbon product is reduced substantially.

The Belgian patent teaches the use of $PdCl_2$ and $PdSO_4$. Although the chloride levels are greatly reduced or supposedly eliminated as compared to the $PdCl_2/CuCl_2$ system, the patent further teaches the use of polyethylsiloxane as a corrosion inhibitor. Thus it is obvious that at these high polyoxoanion concentrations, the corrosion problem of Wacker-type systems has merely been mitigated. The catalyst systems of the instant invention do not contain chloride ions except sometimes as eventual trace contaminants introduced during polyoxoanion synthesis. These systems do not significantly corrode commonly used steels, resulting in substantial capital savings in plant construction.

Vanadium-free heteropolyoxoanion compounds useful in olefin oxidations are disclosed in "Liquid Phase Oxidation of Cyclo-olefins by a $PdSO_4$-Heteropolyacid Catalyst System" by Ogawa, Fujinami, Taya and Teratani, J.C.S. Chem. Comm., 1274–75 (1981). The catalyst system of interest is $PdSO_4—H_3PMo_6W_6O_{40}$ for the oxidation of cyclohexene to cyclohexanone. Very limited conversions were attained, indicating that the reoxidation of $Pd^\circ$ to $Pd^{+2}$ was very inefficient. These systems do not possess commercially viable catalyst lifetimes, especially in view of the high cost of palladium.

The instant invention teaches that the use of a redox active metal component, (and) or a ligand component, in conjunction with the $Pd^{+2}/H_3PMo_6W_6O_{40}$ system improves the conversion and selectivity. However, in the above mentioned particular case of $H_3PMo_6W_6O_{40}$, addition of both a redox active metal component and a ligand increases the oxidation rate by more than two orders of magnitude. This surprising result permits practical application of this catalyst system in an industrial process.

If the redox active metal component is copper, then selectivity to the carbonyl reaction product is greatly improved while copper inhibits the allylic oxidation pathway. This is important in the case of those olefins that have reactive allylic positions, e.g. cyclohexene:

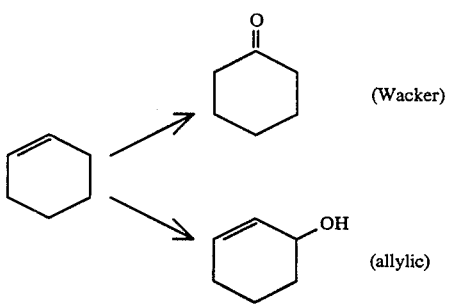

(10)
(Wacker)
(allylic)

U.S. Pat. No. 4,434,082 (Feb. 28, 1984) (hereinafter '082) teaches a Pd+2-heteropolyoxoanion-surfactant system useful in olefin oxidation to ketones. A two phase system is employed consisting of an aqueous phase and a hydrocarbon phase. In such a system, the olefin tends to stay in the hydrocarbon phase and the catalyst in the aqueous phase. As a result, the yields of oxidized product, as shown in Example 6 of the '082 patent, are below three percent for the oxidation of 1-butene to methyl ethyl ketone in the absence of surfactants. To improve the reaction kinetics, the surfactant component is essential for bringing the catalyst and reactants into intimate contact. The instant invention shows improved conversions and selectivities without the use of this surfactant component, identified as essential in the '082 patent.

In sharp contrast to the catalysts of the prior art, the use of the catalyst systems of the instant invention results in a more efficient oxidation process from several important process engineering perspectives. The conversion and selectivity to the desired carbonyl product are greatly improved over earlier systems wherein polyoxoanions were used. Catalyst lifetimes are also enhanced in the present systems. This permits the use of less catalyst, resulting in significant savings. Additionally, the present catalyst systems can be used in a single stage oxidation process, reducing process costs for the energy required to pump and heat the reactants and catalysts, as well as capital equipment costs for the second stage process equipment.

The use of chloride-free components eliminates several major engineering shortcomings of the Wacker systems of the prior art. In particular, chloride-free systems exhibit no corrosivity to the process equipment, making the use of stainless steel process equipment possible. This factor improves process economics substantially because initial capital costs for stainless steel equipment are far below those for titanium-clad or glass-lined vessels. Further, chloride-free systems eliminate many of the problems resulting from chloroorganic by-product formation under oxidation process conditions. The separation and disposal of these undesirable choloroorganic compounds present significant engineering and environmental problems when encountered on an industrial process scale.

The present catalyst systems exhibit higher yields than the prior art when more complex substrates are oxidized. Chloride-containing catalysts show a pronounced and rapid dropoff in yield of the desired carbonyl compounds as the number of carbons in the olefin substrate increases. The formation of complex chloroorganic by-products decreases overall yield to the desired carbonyl product. In the present system, the decrease in yield as a function of the increasing number of carbons in the olefin is less pronounced. This allows the economically attractive production of ketones which could not be produced by prior art catalyst systems.

Therefore, it is one object of this invention to provide an efficient catalyst system for olefin oxidation which eliminates the use of corrosive chloride ions.

It is another object of this invention to provide a catalyst system which possesses economically practicable industrial oxidation rates, conversions and selectivities.

It is yet another object of this invention to eliminate the use of a phase transfer agent or surfactant in the reaction system.

It is a further object of this invention to obtain improved rates and selectivities in the olefin oxidation reaction by the use of a redox active metal component and/or the use of a ligand.

It is another object of this invention to be able to oxidize a large number of olefins which could not be oxidized efficiently previously because of one or more of the following problems: (a) isomerization, (b) chlorinated by-product formation, and (c) oxidation rates which are too low for industrial practice.

SUMMARY OF THE INVENTION

In accordance with the present invention, catalyst systems useful in olefin oxidation to carbonyl compounds are disclosed. The catalyst systems generally comprise at least one polyoxoanion component and a palladium component. Marked improvements in conversion and yield are obtained when redox active metal components and ligands are added to the system, either alternatively or simultaneously.

The polyoxoanions of the present invention are of two general types. Heteropolyoxoanion compounds are disclosed wherein the "hetero" atom is, e.g., phosphorus, which is surrounded by molybdenum, vanadium, tungsten, individually or in combination, and oxygen atoms. The second type of polyoxoanion is an isopolyoxoanion or a mixed isopolyoxoanion of molybdenum, vanadium, tungsten and oxygen atoms.

The palladium component of the catalyst system can be introduced via palladium metal or a chloride-free palladium compound. The redox active metal component of the present invention is generally a metal anion capable of changing its oxidation state under olefin oxidation reaction conditions. Typically, compounds of copper, iron and manganese are useful as the redox active metal component.

The ligands useful in the catalyst system of the present invention are selective from the family of nitrile compounds. The ligand interacts with the palladium component and (or) the redox active metal component, which enables one, in a substantial number of cases, to increase the rate of olefin oxidation, and (or) the selectivity, and (or) the lifetime of the catalyst.

DETAILED DESCRIPTION OF THE INVENTION

A. Theoretical Basis

Figure 1:
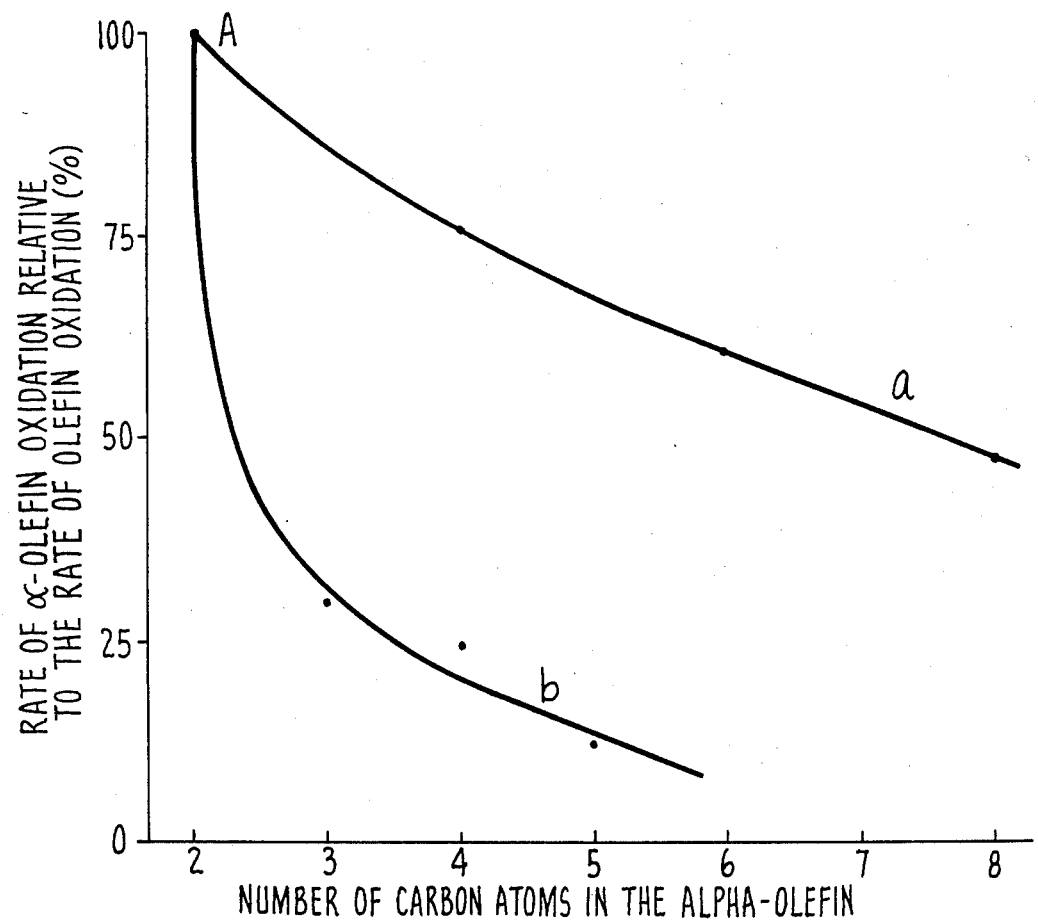
FIG. 1 is a plot of the rate of α-olefin oxidation versus the number of carbon atoms in the α-olefin.

The catalyst utilized according to the instant invention for the oxidation of olefins is made up of the following components: (1) a palladium component; (2) at least one polyoxoanion component; (3) a redox active metal component; and (or) (4) a ligand, where the ligand can complex with either the palladium and (or) with the redox active metal.

The overall general reaction scheme for a representative olefin oxidation can be written as follows:

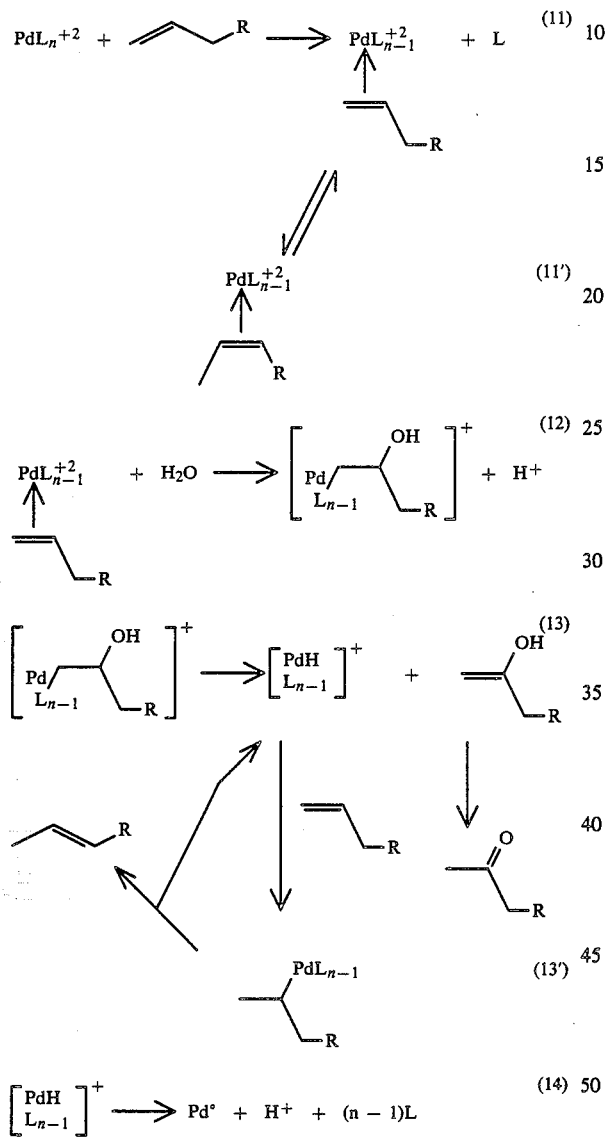

Overall reaction is:

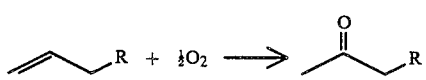

In the above scheme,

represents any olefin, and water is representative of the many nucleophiles which can be used. Ligands L and L' can be the same ligand or can be different ligands. These ligands may include a solvent component or a metal counterion. $M_r^{+q}$ represents the redox active metal component which can undergo a change in oxidation state. $POA^{-p}$ represents any polyoxoanion including their counterions. Similarly, $H^+$ can be generated by any of a number of sources, including, but not limited to acids and water.

Ligand L should possess the following properties. It should complex with palladium (+2) without eliminating the formation of the olefin-$Pd^{+2}$ complex as shown in equation (11). Thus one would expect that ligands L which are not very strong complexors of $Pd^{+2}$, and especially ones which do not have multiple binding sites for $Pd^{+2}$, would be desirable.

Further the ligand L must not reduce the positive charge on $Pd^{+2}$ to the point where reaction (12) becomes too slow. Electron poor ligands which can remove negative charge easily from $Pd^{+2}$ would be preferred ligands.

Ligand L on the other hand should be a strong enough complexor of $Pd^{+2}$ to give additional thermodynamic driving force for reaction (15). In the best case, such a ligand L would stabilize $[PdH]^+$ long enough [Equation (13)] so that it could be oxidized with oxygen before it decomposed to yield palladium metal by reaction (14). It would then allow palladium to be reoxidized without the need for separate reoxidation systems as represented by equations (15) and (16).

As shown above, there is a delicate balance between several effects and only a limited number of ligands L will improve the overall reaction. Others can, and will, slow down or stop the oxidation. The ligands found useful in this invention are described with greater specificity in Section B(4) below.

A $POA^{-p}$ when used by itself must accomplish two functions. First, it must be able to accept electrons from $Pd^\circ$ and oxidize it [Equation (15)]. Then, once reduced, the $POA^{-p-2}$ must be able to reduce oxygen so that the catalytic cycle continues [Equation (16)]. There are a large number of POA's which cannot do both effectively. The redox active metal as shown in the following combination $$[POA^{-p} + M_rL'^{+q}_m]^{-p+q} \qquad (15)$$

is designed to overcome this shortcoming of many of the polyoxoanions. Its function is, either independently, or in conjunction with the polyoxoanion, to improve reaction (15) and (or) reaction (16). Ligand L' has to be chosen in such a way that the thermodynamics (driving force of the reaction) and the kinetics (speed at which the reaction takes place) are both favored. In some cases the same species can act as ligand L for $Pd^{+2}$ and ligand L' for $M_r$.

The above thermodynamic and kinetic requirements can only be met if the ability to transfer electrons between $M_rL'^{+q}_n$ and (or) $POA^{-p}$ and $Pd^\circ$ and (or) $O_2$ exists.

Electrochemistry is one way of analyzing whether the particular $PdL_n^{+2}/POA^{-p}/M_rL'^{+q}_n$ combination is potentially a good catalyst system. Useful combinations preferably have oxidation-reduction potentials (E°$_{\frac{1}{2}}$'s) for

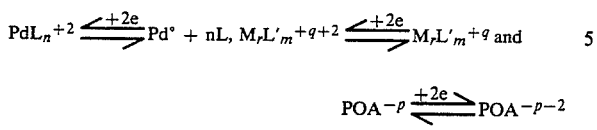

within the potential range of +0.7 VOLT to +0.2 VOLT versus SCE. While the E°$_{\frac{1}{2}}$'s of the individual catalyst components it may not be in the 0.2-0.7 Volt range, the E°$_{\frac{1}{2}}$ of their combination will lie in this range as the result of interactions. Further, the oxidation-reduction potential of

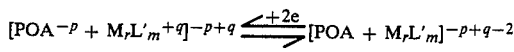

should be chosen to be greater than or close to

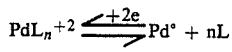

and less than the potential of the reaction

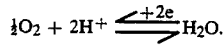

It has been found that the catalyst systems of the present invention are especially effective when the E°$_{\frac{1}{2}}$'s for the individual catalyst components are roughly of the same magnitude, i.e. +0.35±0.1 VOLT versus SCE.

The overall reaction (17) is acid independent. However, some of its component steps [(12), (14), (16)] are acid dependent. Consequently, one may have to adjust the pH (acidity) to obtain the best overall oxidation rate.

Selectivity to the desired carbonyl product can be decreased by side reactions of the olefin such as isomerization by pathways shown in equations (11') and (13'). Overoxidation of the product is also possible.

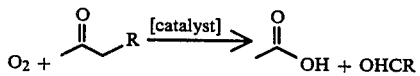

The above side reactions can be catalyzed by the complexes and compounds shown in equations (11) to (16) or by other unidentified catalytic species which form under the reaction conditions.

It can be a further benefit of ligand L, and (or) L', and (or) the redoxactive metal $M_r^{+q}$ that these ligands and metals reduce the rates of some or all of the above undesirable side reactions. For example, by increasing the rate of reaction (12) with respect to the rate of isomerization of

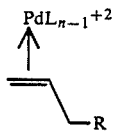

[reaction (11')] a higher selectivity is obtained.

Changing the ligands L and (or) L', and (or) the metal $M_r^{+q}$ will cause one to observe worse or better results, depending on how they affect the various reaction steps (11) to (16) and (18). Thus if one can rapidly eliminate an isomerization catalyst such as $$\begin{bmatrix} PdH \\ L_{n-1} \end{bmatrix}^+$$

by equation (19)

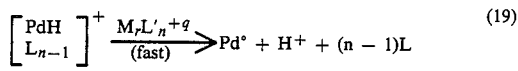 (19)

a better yield to the desired product is the result.

Another example would be if the $[POA^{-p}+M_rL'^{+q}_m]^{-p+q}$ oxidizes

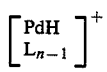

before it decomposes to Pd°. Then increasing the rates of reactions (15) and (or) (16) would reduce isomerization.

In a similar fashion, changing L, and (or) L' and (or) $M_r^{+q}$ will change the amount of other side reactions such as overoxidation.

Optionally, $M_r^{+q}$ and (or) $Pd^{+2}$ can be part of the polyoxoanion structure.

B. Catalyst System

The catalyst system of the present invention generally comprises at least one polyoxoanion component and a palladium component. The addition of a redoxactive metal component, and (or) a ligand increases the conversion of olefin and selectivity to the desired carbonyl product.

(1) The Polyoxoanion Component

The polyoxoanion component of the catalyst system can be either an isopolyoxoanion or heteropolyoxoanion of niobium, tantalum, rhenium, molybdenum, vanadium and tungsten, either in combination or individually. The "hetero" atom can be boron, silicon, germanium, phosphorus, arsenic, selenium, tellurium, iodine, cobalt, manganese or copper. Both polyoxoanion types can be described by the general formula:

wherein
X is a member chosen from the group consisting of B, Si, Ge, P, As, Se, Te, I, Co, Mn and Cu;
M, M' and M" are members independently selected from the group consisting of W, Mo, V, Nb, Ta and Re;
x is zero for isopolyoxoanions and mixed isopolyoxoanions or x is an integer for heteropolyoxoanions;
a, b, c, m and z are integers; and a+b+c≧2.
Several sub-genera of polyoxoanions have also been developed to describe the polyoxoanion components of the instant invention.

I. Isopolyoxoanions

A. General

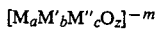

wherein
- M, M' and M" are members independently selected from the group consisting of W, Mo, V, Nb, Ta and Re;
- z and m are integers greater than zero;
- a, b and c are integers; and
- $a+b+c \geq 2$;

B. Molybdenum $$[Mo_a M'_b M''_c O_z]^{-m}$$

wherein M' and M" are members independently selected from the group consisting of W, V, Nb, Ta and Re;
- a, z and m are integers greater than zero;
- b and c are integers; and
- $a+b+c \geq 2$;

C. Tungsten $$[W_a M'_b M''_c O_z]^{-m}$$

wherein
- M' and M" are members independently selected from the group consisting of Mo, V, Nb, Ta and Re;
- a, z and m are integers greater than zero;
- b, c are integers; and
- $a+b+c \geq 2$;

D. Vanadium $$[V_a M'_b M''_c O_z]^{-m}$$

wherein
- M' and M" are members independently selected from the group consisting of W, Mo, Nb, Ta and Re;
- a, z and m are integers greater than zero;
- b, c are integers; and
- $a+b+c \geq 2$;

II. Heteropolyoxoanions

A. General $$[X_x M_a M'_b M''_c O_z]^{-m}$$

wherein
- X is a member selected from the group consisting of B, Si, Ge, P, As, Se, Te, I, Co, Mn and Cu;
- M, M' and M" are members independently selected from the group consisting of W, Mo, V, Nb, Ta, Re;
- a, x, z and m are integers greater than zero;
- b, c are integers; and
- $a+b+c \geq 2$;

B. Molybdenum $$[X_x Mo_a M'_b M''_c O_z]^{-m}$$

wherein X is a member selected from the group consisting of B, Si, Ge, P, As, Se, Te, I, Co, Mn and Cu;
- M' and M" are members independently selected from the group consisting of W, V, Nb, Ta and Re;
- a, x, z and m are integers greater than zero;
- b, c are integers; and
- $a+b+c \geq 2$;

C. Tungsten $$[X_x W_a M'_b M''_c O_z]^{-m}$$

wherein
- X is a member selected from the group consisting of B, Si, Ge, P, As, Se, Te, I, Co, Mn and Cu;
- M' and M" are members independently selected from the group consisting of Mo, V, Nb, Ta and Re;
- a, x, z and m are integers greater than zero;
- b, c are integers; and
- $a+b+c \geq 2$;

D. Vanadium $$[X_x V_a M'_b M''_c O_z]^{-m}$$

wherein
- X is a member selected from the group consisting of B, Si, Ge, P, As, Se, Te, I, Co, Mn and Cu;
- M' and M" are members independently selected from the group consisting of W, Mo, Nb, Ta and Re;
- a, x, z and m are integers greater than zero;
- b, c are integers; and
- $a+b+c \geq 2$;

Examples of typical polyoxoanion species are as follows:

(a) Heteropolyoxoanions $[PMo_6 V_6 O_{40}]^{-9}$ $[PMo_4 V_8 O_{40}]^{-11}$ $[PMo_8 V_4 O_{40}]^{-7}$ $[P_2 W_{12} Mo_5 V O_{62}]^{-7}$ $[P_2 W_{15} Mo_2 V O_{62}]^{-7}$ (b) Isopolyoxoanions $[Mo_4 V_8 O_{36}]^{-8}$ $[Mo_3 V_3 O_{19}]^{-5}$ $[Mo_6 V_2 O_{26}]^{-6}$ $[Mo_6 V_6 O_{36}]^{-6}$ $[W_7 Mo_3 V_2 O_{36}]^{-2}$ $[Mo_8 V_4 O_{36}]^{-4}$ (c) Vanadium-free polyoxoanions $[P_2 Mo_{18} O_{62}]^{-6}$ $[P_2 Mo_6 W_{12} O_{62}]^{-6}$ $[PMo_6 W_6 O_{40}]^{-3}$ $[P_2 Mo_5 O_{23}]^{-6}$ $[Mo_6 W_6 O_{41}]^{-10}$ (d) Molybdenum-free polyoxoanions $[PV_{14} O_{42}]^{-9}$ $[PWV_{11} O_{40}]^{-14}$ $[PW_6 V_6 O_{40}]^{-9}$ $[PW_8 V_4 O_{40}]^{-7}$ $[P_2 W_{12} V_6 O_{62}]^{-12}$ $[P_2 W_{15} V_3 O_{62}]^{-9}$ $[W_6 V_6 O_{36}]^{-6}$ It is to be recognized, by one skilled in the art, that even though a particular stoichiometric ratio for the preparation of a polyoxoanion may correspond to the above identified species, the actual species present in either the crystalline form or in situ, may differ from those identified above. Rather, the crystals, or in situ preparation, are likely to contain a mixture of many different species of the polyoxoanion. Thus, although sometimes not immediately isolable, all species formed when the polyoxoanions described above are prepared and used are intended to be within the scope of this invention.

It is also intended to be within the scope of this invention to use a mixture of polyoxoanions as the polyoxoanion component of the inventive catalyst system. In certain cases, the mixture of polyoxoanions may produce catalytic activity possessed by none of the mixture's individual polyoxoanion components. It will also be recognized, by one skilled in the art, that just as certain mixtures of polyoxoanions result in improved results, there are other mixtures which detract from the catalyst activity of the individual components.

Although the above generic and sub-generic descriptions cover all of the species which are useful in this catalyst system, several broader subgenera have been identified which exhibit unexpected catalyst activity. For example, catalyst systems comprising molybdenum-free polyoxoanions, or vanadium-free polyoxoanions, have been demonstrated to provide the necessary catalyst activity to obtain improved conversions and selectivities.

Countercations for the polyoxoanions can be protons, alkali metal cations, alkaline earth cations, transition metal cations, including cations of Pd, Cu, Co and Mn, and organic cations. Preferred cations for use in the present catalyst system include protons, Cu, Na, K and Li.

The amount of polyoxoanion used has to be large enough so that the reoxidation of $Pd^\circ$ to $Pd^{+2}$ is not rate limiting for the overall oxidation reaction. Yet, the amounts of polyoxoanion must be low enough to be cost effective while simultaneously giving reaction solutions of reasonable viscosity.

(2) Palladium Component

Any palladium containing material, or mixtures thereof, which are suitable for catalytic oxidation of olefins can be used in the catalyst system of the present invention. Finely divided palladium metal powder, palladium metal, and essentially chloride-free palladium compounds are all useful in the present invention, either individually or in combination. The preferred compounds are palladium trifluoroacetate, $Pd(CF_3COO)_2$; palladium acetate, $Pd(CH_3COO)_2$; palladium sulfate, $PdSO_4$; and palladium nitrate, $Pd(NO_3)_2$. Although chloride-free palladium salts are preferred, it is intended to be within the scope of this invention to use palladium chloride.

(3) Redox Active Metal Component

Any metal component which is capable of undergoing a change in valence under the reaction conditions of olefin oxidation, or mixtures thereof, can be used in the catalyst system of the present invention. The counteranion to this redox active metal should not contain chlorides. Preferred redox active metal components include cupric (cuprous) sulfate, $CuSO_4$; cupric acetate, $Cu(CH_3COO)_2$; cupric nitrate $Cu(NO_3)_2$, and ferrous (or ferric) acetate, $Fe(CH_3COO)_2$; ferrous (or ferric) sulfate, $FeSO_4$.

(4) Ligands

Since the ligand compounds serve a number of functions there are a limited number of them. A class of compounds which are useful in the instant invention are the family of nitriles ($RC\equiv N$), including benzonitrile. The preferred ligand is acetonitrile.

C. Olefin Oxidation Process

(1) Substrates

The olefinic hydrocarbon reactant, or substrate, which is oxidized according to the process of the instant invention is basically any hydrocarbon containing at least one carbon-carbon double bond, or mixtures of such hydrocarbons. The olefinic hydrocarbon, which contains at least two carbon atoms per molecule, can be either substituted (e.g., 4-methyl, 1-pentene) or unsubstituted (e.g., 1-pentene), and either cyclic (e.g., cyclohexene) or acyclic (e.g., 2-hexene). If the olefinic hydrocarbon is acyclic, the carbon-carbon double bond can be either terminal (so-called alpha-olefins) or non-terminal (so-called internal olefins). If the olefinic hydrocarbon contains more than one carbon-carbon double bond, the double bonds can be conjugated or unconjugated. No particular upper limit applies to the carbon number of the olefinic hydrocarbon. However, a practical limitation is that both the reactivity of the hydrocarbon and the selectivity to the carbonyl compound(s), in general, tend to decrease with increasing carbon number. The decrease in selectivity is partially due to the increased isomerization tendency of higher olefins. One feature of the present invention is that the decrease in reactivity and selectivity resulting from increasing the carbon number is much less dramatic than is found in prior art. This is achieved through a delicate balance of the concentration and type of redox active metal and (or) ligand and stirring efficiency (reactor design). Thus oxidation of higher olefins appears commercially practical.

Olefinic hydrocarbons exhibit different reactivities depending on their structure. As a general rule, acyclic terminal olefins react faster than acyclic internal olefins, acyclic olefins react faster than cyclic olefins, and unsubstituted olefins react faster than substituted olefins. Exceptions to that rule which have been observed under the conditions of the present invention are: 2-butene reacts faster than 1-butene; cyclohexene reacts faster than 1-hexene. Preferred olefinic hydrocarbons are therefore unsubstituted terminal mono olefins, such as ethylene, propylene, 1-butene, 1-hexene, 1-octene, 1-decene, 1-dodecene, 1-octadecene, 1-eicosene and higher terminal mono olefins, unsubstituted beta-olefins, such as 2-butene, 2-pentene, 2-hexene, 2-octene, and higher beta-olefins, and cyclic olefins, such as cyclohexene, 3-methyl 1-cyclohexene and many others.

(2) Solvent

Since the solvent is present in large excess compared to the catalyst components, one must select a solvent that does not affect the catalyst system adversely. Solvents of choice are water or water/ligand mixtures. Other solvents potentially can be used if the catalyst components remain active.

(3) Acid Component pH or acidity can be adjusted by various proton sources, such as an acid form of a polyoxoanion or an inorganic acid like $HBF_4$, $HNO_3$, or $H_2SO_4$. In some cases an organic acid like acetic acid may be acceptable. A preferred acid is sulfuric acid.

(4) Oxygen

Depending on the process one can use either air or oxygen. Other sources of oxygen are acceptable but would be less economical. Similarly other oxidants would be acceptable but are anticipated to be less economical.

(5) Stirring Speed

The product distribution in an oxidation can be highly dependent on the stirring speed in the reactor. Since the reactions tend to be multiphase, the rate limiting step can be the supply of a reagent to the catalyst (e.g, oxygen or olefin). Increasing the stirring speed can increase the mass transport of the reactants to the catalyst and/or the mass transport of products from the catalyst into the bulk solution. Depending on the intermediate species in the rate determining steps leading to the various products, the ratio of these products can change as a function of the mass transport. In the catalyst systems of the instant invention it has been observed in many cases that increasing the stirring speed dramatically increases the oxidation rate over the isomerization rate. The oxidation rate is increased by the higher oxygen concentration while the isomerization appears to be independent of the oxygen and the olefin concentration.

(6) Process Conditions

The optimum temperature for the olefin oxidation reaction can vary depending upon the individual olefin substrate. Low molecular weight liquid olefins become increasingly volatile at higher temperatures. High reaction temperatures may not be desired in view of the increased volatility. The reaction temperature is typically between 20° C. and 175° C., preferably 65° C. to 90° C. At lower temperatures the rate of oxidation becomes too slow and at higher temperatures overoxidation can be a problem. In the case of nitriles, hydrolysis to amides and acids can be problematic above 85° C.

The operating pressure for the oxidation reaction is typically between 0–200 psig. At lower pressures the rate of oxidation can be too slow while at higher pressures the risks of overoxidation and explosion increase.

The pH of the liquid phase is maintained between 0 and 7, preferably between 1 and 3, by the addition of appropriate amounts of $H_2SO_4$. Both at lower and at higher pH the polyoxoanions tend to decompose.

The ratio of Pd/polyoxoanion/redox active metal varies from 1/0.5/0.2 to 1/50/500 but preferably lies around 1/5/10.

The amount of ligand present can vary from 1 mole/mole of palladium (and) or redox active metal to where it is the main component of the solvent. The optimum varies for different olefins and different heteropolyoxoanion systems.

Reaction times vary from a few minutes to 48 hours. Short reaction times can lead to heat management problems while long reaction times lead to economically unattractive large reactor sizes.

D. Working Examples

The examples set forth below fall into two major categories. Examples I–XXVI illustrate some of the methods used to prepare the polyoxoanion components of the instant invention. In some cases the preparations were specially developed for this invention and in other cases the methods used are analogous to methods of preparation published in the open literature (R. Massart et al., Inorg. Chem., 16, 2916 (1977); A. Bjornberg, Acta Cryst., B35, 1995 (1979); Misono et al., Bull. Chem. Soc. Jap., 55, 400 (1982); R. Strandberg, Acta Chem. Scand., 27, 1004 (1973); B. Dawson, Acta Cryst., 6, 113–126 (1953); M. Droege, Ph.D. Dissertation, University of Oregon, (1984); R. Constant et al., J. Chem. Res., p. 222(s) and p. 2601–2617(m) (1977)). Wherever possible, the synthesis of the polyoxoanion was done in the absence of chloride ions. In some cases, chloride ions were present in order to form and (or) crystallize the desired structure. In these cases, it was shown by analysis that only trace amounts of chloride were present.

The second category, Examples XXVII–XLII, pertains to the oxidation process itself.

EXAMPLE I

$K_9PMo_6V_6O_{40}$

The preparation of this heteropolyoxoanion is based on the one described in Smith, Pope "Inorganic Chemistry", Volume 12, page 331 (1973).

In a first flask, 73.2 grams of sodium meta vanadate ($NaVO_3$) were dissolved in 380 ml of distilled water which had been heated to 90° C. 80.7 grams of sodium molybdate ($Na_2MoO_4 \cdot 2H_2O$) were added to 120 ml of distilled water contained in a second, round bottom flask. This molybdate solution was heated to 90° C. and stirred. The vanadate solution in the first flask was added to the round bottom flask which was then fitted with a reflux condenser. The solution in the round bottom flask turned yellow-orange. 50 ml of 85% phosphoric acid ($H_3PO_4$) were added dropwise to the yellow-orange solution which turned it very dark. The solution was heated to 95° C. for 1 hour and then filtered through Celite  (Johns-Manville Corp., Denver, Colo.). The Celite ® was washed with a small amount of cold water.

Approximately 80 grams of potassium sulfate ($K_2SO_4$) were added to the filtrate which had been cooled to room temperature. The solution was stirred for one to one and one-half hours. The precipitate which had formed was collected and dried in a vacuum oven. The solid was recrystallized from 120 ml of 0.25M sulfuric acid ($H_2SO_4$). The crystals were dried in a vacuum oven.

The potassium salt $K_9PMo_6V_6O_{40}$ was used to prepare a lithium salt $Li_9PMo_6V_6O_{40}$ by ion-exchange chromatography. The acid form of an Amberlyst ® (Rohm & Haas, Philadelphia, Pa.) ion-exchange resin was exchanged to the $Li^+$ form by eluting with 1M lithium hydroxide (LiOH). After washing the column free of excess hydroxide the acid form of $PMo_6V_6O_{40}^{-9}$ was slowly eluted down the column with water. Removal of water yielded the more soluble lithium salt of $PMo_6V_6O_{40}^{-9}$.

EXAMPLE II

$Na_{11}PMo_4V_8O_{40}$

The preparation of this heteropolyoxoanion is based on the one described in S. F. Davison's Ph.D. Dissertation, University of Sheffield (1982).

5.7 grams sodium phosphate ($Na_3PO_4 \cdot 12H_2O$), 8.64 grams molybdenum trioxide ($MoO_3$), 14.74 grams of vanadium pentoxide ($V_2O_5$) and 2.41 grams of sodium carbonate ($Na_2CO_3$) were added to 75 ml of distilled water in a one neck, round bottom flask. The solution was heated to reflux and kept there for one hour. The resulting red solution was filtered through Celite ®. The filtrate volume was reduced on a rotovap and the sodium salt $Na_{11}PMo_4V_8O_{40}$ was crystallized from the remaining liquid by cooling.

EXAMPLE III

$Na_7PMo_8V_4O_{40}$

The preparation of this heteropolyoxoanion is based on the one described in S. F. Davison's Ph.D. dissertation, University of Sheffield (1982). 5.7 grams sodium phosphate ($Na_3PO_4.12H_2O$), 17.25 grams molybdenum oxide ($MoO_3$), 6.3 grams vanadium pentoxide ($V_2O_5$) and 2.41 grams sodium carbonate ($Na_2CO_3$) were added to 75 ml of water in a one neck, round bottom flask. The solution was heated to reflux and refluxed for one hour. The resulting red solution was filtered through Celite ®. The filtrate volume was reduced on a rotary evaporation and the sodium salt $Na_7PMo_8V_4O_{40}$ was crystallized from the remaining liquid by cooling.

EXAMPLE IV

$P_2W_{12}Mo_5VO_{62}{}^{-7}$

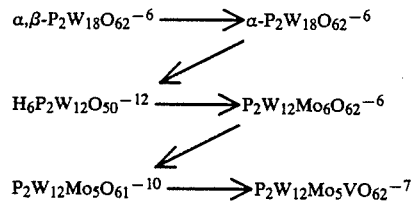

a. $K_6[\alpha,\beta\text{-}P_2W_{18}O_{62}]$

The preparation of this polyoxoanion is based upon the one described in B. Dawson, Acta Cryst. 6, 113–126 (1953). 400 grams of sodium tungstate ($Na_2WO_4.2H_2O$) was added to 700 ml of boiling distilled water. 85% phosphoric acid ($H_3PO_4$) was added dropwise to the boiling solution. The solution turned light green during the dropwise addition. The entire mixture was refluxed for approximately eight hours. After cooling to room temperature, 100 grams of potassium sulfate ($K_2SO_4$) was added. The solution was left to crystallize for several hours. The solid, a green-yellow precipitate of the formula $K_6[\alpha,\beta\text{-}P_2W_{18}O_{62}]$, was collected. The filtrate was discarded.

b. $K_6[\alpha\text{-}P_2W_{18}O_{62}]$

The preparation of this polyoxoanion is based on the one described in M. Droege, Ph.D. Dissertation, University of Oregon (1984). 160 grams of the potassium salt $K_6[\alpha,\beta\text{-}P_2W_{18}O_{62}]$ was dissolved in 500 ml of distilled water contained in a two-liter flask. The solution was heated gently to dissolve all of the solids. After all of the solids were dissolved, the solution was cooled to room temperature. A 10% potassium bicarbonate (KHCO$_3$) solution was added via an addition funnel. After the addition of 150 ml of potassium bicarbonate a precipitate formed. Upon further addition of 450 ml the solid dissolved and the solution was colorless. Next, 320 ml of 6N sulfuric acid was added in 10 ml aliquots, to regenerate the anion $\alpha\text{-}P_2W_{18}O_{62}{}^{-6}$. After all of the sulfuric acid had been added, the solution was yellow-green with slight precipitation. The solution was filtered through Celite ®. 50 grams of potassium sulfate were added to the filtrate and a precipitate appeared immediately. The precipitate $K_6[\alpha\text{-}P_2W_{18}O_{62}]$ was collected, washed and dried in an oven.

c. $K_{12}H_6P_2W_{12}O_{50}$

The preparation of this polyoxoanion is based on the one described in R. Contant et al., J. Chem. Res., 222(s), 23601–2617(m) (1977). 80 grams of the potassium salt $K_6[\alpha\text{-}P_2W_{18}O_{62}]$ were dissolved in 500 ml of water and 200 ml of a 2M tris [(HOCH$_2$)$_3$CNH$_2$] buffer solution and left to stir for thirty minutes. About 40 grams of potassium sulfate and 200 ml of 2M potassium carbonate ($K_2CO_3$) were added to the solution and the white precipitate $K_{12}H_6P_2W_{12}O_{50}$ appeared. The solution was cooled to 10° C. and filtered. The product was washed with saturated potassium sulfate and then dried in a vacuum oven.

d. $K_6P_2W_{12}Mo_6O_{62}$

The preparation of this polyoxoanion is based on the one described in R. Massart et al., Inorg. Chem., 16, 2916 (1974). About 75 grams of the potassium salt $K_{12}H_6P_2W_{12}O_{50}$ was added to 75 ml of 1M lithium chloride (LiCl) and was acidified to pH 2 with 1N hydrochloric acid. Additional lithium chloride was added, but the potassium salt was still somewhat insoluble. Next 15.7 grams of lithium molybdate (Li$_2$MoO$_4$) was added to the solution which then became bright yellow and almost clear. The solution was again acidified with 1N hydrochloric acid to pH 4.5. Precipitation occurred upon cooling. The precipitate, potassium and lithium salts of the anion $P_2W_{12}Mo_6O_{62}{}^{-6}$, was collected, washed and dried. The precipitate was recrystallized from 100 ml of 0.1N sulfuric acid to remove traces of chloride and to obtain the potassium form $K_6P_2W_{12}Mo_6O_{62}$. In its hydrated form, the salt has the formula $K_6P_2W_{12}Mo_6O_{62}.14H_2O$.

e. $K_{10}P_2W_{12}Mo_5O_{61}.20H_2O$, $K_7P_2W_{12}Mo_5VO_{62}$ 40 grams of the potassium salt $K_6P_2W_{12}Mo_6O_{62}.14\text{-}H_2O$ was dissolved in 140 ml of water and then was treated with 80 ml of 1M potassium bicarbonate (KHCO$_3$). A white-yellow precipitate was collected and crystallized from 30 ml of hot water. The white precipitate has the general formula $K_{10}P_2W_{12}Mo_5O_{61}.20H_2O$.

10 grams of the potassium hydrate $K_{10}P_2W_{12}Mo_5O_{61}.20H_2O$ were dissolved in 40 ml of distilled water and was vigorously stirred. 2.2 ml of 1M lithium vanadate (LiVO$_3$), 10 ml of 1M hydrochloric acid and 2.7 ml of concentrated 12M hydrochloric acid were added consecutively to the solution. Then, 11 grams of potassium chloride were added. A bright orange precipitate $K_7P_2W_{12}Mo_5VO_{62}$ was collected and air dried.

EXAMPLE V  $H_7P_2W_{15}Mo_2VO_{62}$

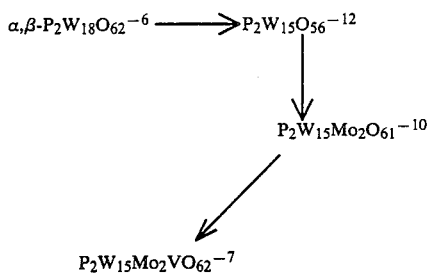

a. $Na_{12}P_2W_{15}O_{56}$

The preparation of this polyoxoanion is based on the one described in M. Droege, Ph.D. Dissertation, University of Oregon (1984). 80 grams of the potassium salt $K_6[\alpha-P_2W_{18}O_{62}]$ were dissolved in 267 ml of water. Next, 107 grams of sodium perchlorate (NaClO$_4$) were added. The light-green solution was stirred for 2 hours; the insoluble precipitate potassium perchlorate (KClO$_4$) was filtered off. About 200 ml of 1M sodium carbonate (Na$_2$CO$_3$) was added to the filtrate to obtain a pH of 9. The solution was essentially colorless at this point. A white solid, $Na_{12}P_2W_{15}O_{56}$, precipitated and was collected. The precipitate was washed with sodium chloride (NaCl) solution, ethanol and diethyl ether [(CH$_3$CH$_2$)$_2$O], and then was dried for eight hours at 60° C.

b. $P_2W_{15}Mo_2O_{61}^{-10}$

To 150 ml of an aqueous solution containing 0.013 moles of sodium molybdate hydrate (Na$_2$MoO$_4$.2H$_2$O) and 11 ml of 1M HCl was added 10 grams of the potassium salt $K_{12}P_2W_{15}O_{56}$. The solution was stirred until clear. 1M HCl was then added dropwise until the pH was 6–6.5. Then 7 grams of potassium chloride KCl was added. A white precipitate $K_{10}P_2W_{15}Mo_2O_{61}$ resulted and was filtered, washed and dried.

c. $P_2W_{15}Mo_2VO_{62}^{-7}$ 13.5 grams of the potassium salt $K_{10}P_2W_{15}Mo_2O_{61}$ was dissolved in 50 ml of water. The solution was vigorously stirred while in the following order 0.35 g of lithium vanadate (LiVO$_3$), 25 ml of 1M hydrochloric acid and about 4 ml of concentrated hydrochloric acid were added. The solution turned yellow with the addition of lithium vanadate. Potassium chloride was added to cause precipitation of the potassium salt $K_7P_2W_{15}Mo_2VO_{62}$.

EXAMPLE VI

$K_8Mo_4V_8O_{36}$

The preparation of this isopolyoxoanion is based on the preparation described by A. Bjornberg, Acta Cryst. 1979, B35, p. 1989. 14.40 grams of molybdenum trioxide (MoO$_3$) was added to 200 ml of 0.5M KOH. A white suspension was obtained. 23.40 grams of ammonium meta vanadate (NH$_4$VO$_3$) was mixed with 240 ml of distilled water. The above two slurries were mixed. While stirring vigorously 50 ml of 2M H$_2$SO$_4$ was added until the pH was ~1.5–2.0. A red-orange color formed as the solids reacted and dissolved in the solution. Next, 35 grams of potassium sulfate (K$_2$SO$_4$) was added and the volume of the solution was reduced by two-thirds by the removal of water under vacuum. The resulting solution was left in a refrigerator overnight to crystallize. The salt $K_8Mo_4V_8O_{36}$ was filtered and dried in a vacuum oven at 40° C.

EXAMPLE VII

$K_5Mo_3V_3O_{19}$ 20.0 grams of sodium molybdate (Na$_2$MoO$_4$.2H$_2$O) and 10.08 grams of sodium vanadate (NaVO$_3$) were added to an acetate buffer of pH 6.4. Potassium chloride was added to precipitate the isopolyoxoanion $K_5Mo_3V_3O_{19}$ which was filtered, washed, and dried.

EXAMPLE VIII

$Na_6Mo_6V_2O_{26}.16H_2O$

This preparation was based on the one described in Bjornberg, Acta Cryst. 1979, B35, p. 1995. 6.1 grams of sodium vanadate (NaVO$_3$) was dissolved in 150 ml of hot distilled water. In a second flask, 36.3 grams of sodium molybdate (Na$_2$MoO$_4$.2H$_2$O) was dissolved in 150 ml of hot distilled water. The two solutions were mixed. 66.65 ml of 3M HCl was added dropwise while the solution was vigorously stirred. Then 30 grams of NaCl was added to the solution. A solid $Na_6Mo_6V_2O_{26}.16H_2O$ formed and was filtered and dried.

EXAMPLE IX

$[Mo_4V_8O_{36}]^{-8}$

This is an in situ preparation. Two separate solutions of 2.24 grams of sodium molybdate (Na$_2$MoO$_4$.2H$_2$O) and 2.25 grams of sodium meta vanadate (NaVO$_3$) were mixed and diluted to 50 ml with distilled water. 5 ml of the above solution were pipetted into 11.5 ml of reaction solvent containing 1.73 mmole of sulfuric acid (H$_2$SO$_4$). The pH of the solution was 1.6. The reaction solution had turned orange because the isopolyoxoanion $[Mo_4V_8O_{36}]^{-6}$ had formed.

EXAMPLE X

$[Mo_6V_6O_{36}]^{-6}$

This is a simplex preparation, also known as in situ. 0.354 grams of sodium vanadate (NaVO$_3$) were dissolved in 30 ml of distilled water. Next, 0.702 grams of sodium molybdate (Na$_2$MoO$_4$.2H$_2$O) was added. The pH of the resulting solution was adjusted to 1.6 with concentrated H$_2$SO$_4$. The final volume was adjusted to 36 ml by addition of distilled water. The polyoxoanion $[Mo_6V_6O_{36}]^{-6}$ was present in the aqueous solution.

EXAMPLE XI

$[Mo_8V_4O_{36}]^{-4}$ 0.9368 grams of sodium molybdate (Na$_2$MoO$_4$.2H$_2$O) and 0.2361 grams of sodium vanadate (NaVO$_3$) were dissolved in 36 ml of distilled water. The pH of the solution was adjusted to 1.6 by the addition of concentrated H$_2$SO$_4$. The polyoxoanion $[Mo_8V_4O_{36}]^{-4}$ was present in solution and was used in the olefin oxidation reactions.

EXAMPLE XII

$[W_2Mo_6V_4O_{36}]^{-4}$

This isopolyoxoanion was made by an in situ method. 1.52 grams of sodium tungstate (Na$_2$WO$_4$.2H$_2$O) was dissolved in 10 ml of distilled water. 1.126 grams of sodium meta vanadate (NaVO$_3$) was dissolved in another 10 ml of hot distilled water. 3.35 grams of sodium molybdate ($Na_2MoO_4.2H_2O$) was dissolved in yet a third 10 ml of distilled water. The three solutions were combined and diluted to 50 ml with additional distilled water. The solution was acidified to pH 2 with 0.78 ml of 5N sulfuric acid. This solution now contained $[W_2Mo_6V_4O_{36}]^{-4}$ and was used in the olefin oxidation reactions.

EXAMPLE XIII $[W_6Mo_2V_4O_{36}]^{-4}$

This is an in situ preparation. Three separate solutions containing 4.57 grams of sodium tungstate ($Na_2WO_4.2H_2O$), 1.12 grams of sodium molybdate ($Na_2MoO_4.2H_2O$) and 1.13 grams of sodium meta vanadate ($NaVO_3$), respectively, were mixed and diluted to 50 ml with distilled water. The isopolyoxoanion $[W_6Mo_2V_4O_{36}]^{-4}$ was formed by pipetting 5.0 ml of the above mixture into 11.5 ml of reaction solvent containing 2.60 mmole of sulfuric acid. The pH was maintained at ~1.6.

EXAMPLE XIV $[W_7Mo_3V_2O_{36}]^{-2}$ 1.13 grams of sodium tungstate ($Na_2WO_4.2H_2O$), 0.408 grams of sodium molybdate ($Na_2MoO_4.2H_2O$) and 0.085 grams of sodium vanadate ($NaVO_3$) were added to 36 ml of distilled water. The pH of the resulting solution was adjusted to 1.6 with concentrated sulfuric acid. The isopolyoxoanion $[W_7Mo_3V_2O_{36}]^{-2}$ was present in the solution.

EXAMPLE XV $[W_6V_6O_{36}]^{-6}$ 4.57 grams of sodium tungstate ($Na_2WO_4.2H_2O$) was dissolved in 20 ml of distilled water. 1.69 grams of sodium vanadate ($NaVO_3$) was dissolved in 20 ml of hot distilled water. The two solutions were combined and diluted to 50 ml. The isopolyoxoanion $[W_6V_6O_{36}]^{-6}$ was formed by pipetting 5.0 ml of the above solution into 11.5 ml of reaction solvent containing 3.20 mmole of sulfuric acid ($H_2SO_4$). The pH was ~1.6.

EXAMPLE XVI $Na_6P_2Mo_{18}O_{62}$

This preparation is based on the one described in Rene Massart et. al., Inorganic Chemistry, 16, 2916 (1977).

18 grams sodium monohydrogen phosphate as the hydrate ($Na_2HPO_4.12H_2O$) was dissolved in a mixture of 73 ml of 11.7N perchloric acid ($HClO_4$) and 20 ml of water. A solution of 108 grams of sodium molybdate dihydrate ($Na_2MoO_4.2H_2O$) in 200 ml of water was added dropwise to the first solution. A yellow precipitate formed. Heating the solution changed the color to orange. The solid $Na_6P_2Mo_{18}O_{62}$ crystallized and was separated, washed, and dried.

EXAMPLE XVII $K_6P_2W_{12}Mo_6O_{62}$

See Example IV-a,b,c,d for the preparation of $K_6P_2W_{12}Mo_6O_{62}$.

EXAMPLE XVIII $Na_3PMo_6W_6O_{40}$, $H_3PMo_6W_6O_{40}$, $Li_3PMo_6W_6O_{40}$

This preparation is based on the one described in Misono et al., Bull. Chem. Soc. Jap., 55, 400 (1982). 45 grams of sodium tungstate dihydrate ($Na_2WO_4.2H_2O$), 33 grams of sodium molybdate dihydrate ($Na_2MoO_4.2H_2O$) and 12.25 grams of sodium monohydrogen phosphate septa hydrate ($Na_2HPO_4.12H_2O$) were dissolved in 200 ml of distilled water and the solution was heated to 80° C. for three hours with stirring. The solution volume was reduced to about 50 ml by use of a rotary evaporator. A white precipitate appeared. The precipitate was redissolved by the addition of about 40 ml of water. A yellow precipitate, the sodium salt $Na_3PMo_6W_6O_{42}$, was formed when the solution was acidified by the addition of 100 ml of 24% hydrochloric acid. The precipitate was collected, washed and dried in a vacuum oven.

The sodium salt solution was slowly eluted down a cation ion exchange column which was in the H+ form. The water eluate was extracted with ether. The ether was evaporated leaving $H_3PMo_6W_6O_{40}$.

The acid form of an Amberlyst ® resin was converted to the Li+ form by treatment with lithium hydroxide (LiOH). The excess lithium hydroxide was washed out. An aqueous solution of $Na_3PMo_6W_6O_{40}$ was eluted slowly down the column. The lithium salt was obtained by reducing the volume of eluant which led to the crystallization of $Li_3PMo_6W_6O_{40}$.

EXAMPLE XIX $H_6P_2Mo_5O_{23}$

The preparation is based on the one described in R. Strandberg, Acta. Chem. Scand., 27, 1004 (1973). 74 grams of sodium molybdate dihydrate ($Na_2MoO_4.2H_2O$) and 14.76 grams of sodium dihydrogenphosphate ($NaH_2PO_4$) were dissolved in 150 ml of distilled water. 31.5 ml of 11.7M perchloric acid ($HClO_4$) were added to the solution. The resulting solution was poured into a crystallizing dish, was covered and set aside until $H_6P_2Mo_5O_{23}$ crystallized. The product was filtered and dried.

EXAMPLE XX $[Mo_6W_6O_{41}]^{-10}$

This isopolyoxoanion is prepared according to the simplex method, or in situ. 0.7026 g of sodium molybdate ($Na_2MoO_4.2H_2O$) and 0.9580 g of sodium tungstate ($Na_2WO_4.2H_2O$) were dissolved in 36 ml of distilled water. The pH was adjusted to 1.6 with concentrated sulfuric acid. The species $[Mo_6W_6O_{36}]$ is present in the resulting solution.

EXAMPLE XXI $H_9PV_{14}O_{42}$, $Na_9PV_{14}O_{42}$

The preparation of these heteropolyoxoanions is based on the preparation described by Kato N., et al., Inorg. Chem., 21, p. 240 (1982). 90 grams of sodium vanadate ($NaVO_3$) were dissolved in about 500 ml of boiling distilled water. As the solution cooled to room temperature, 25 ml of 7.4M phosphoric acid ($H_2PO_4$) was added dropwise. The pH was adjusted to 1.7 with 100 ml of 3.4M nitric acid ($HNO_3$). A dark-brown-red precipitate, the acid and sodium salts of $PV_{14}O_{42}^{-9}$, formed. The solution was left to cool to further crystallize the vanadium compounds. The crystals were filtered, washed and dried.

EXAMPLE XXII $PMV_{11}O_{40}^{-14}$, $PWV_{12}O_{41}^{-11}$

See Example XXIII below for their preparation.

EXAMPLE XXIII

$K_5H_4PW_6V_6O_{40}$

The preparation of this heteropolyoxoanion is based on the preparation described in D. P. Smith's Ph.D. dissertation, Georgetown University (1975). In a three-neck, round bottom flask, 110 grams of sodium tungstate ($Na_2WO_4.2H_2O$) was added to 120 ml of distilled water and the solution was heated to 85° C. 73.2 grams of sodium vanadate ($NaVO_3$) was added to 380 ml of distilled water which had been preheated to 90° C. The two hot solutions were combined in the round bottom flask, and were kept at 90° C. 50 ml of 85% phosphoric acid was added dropwise, turning the orange-gold solution to a black-red color. The solution was maintained at 95° C. for one hour.

The solution was then filtered through Celite ® and the filtrate was allowed to cool to room temperature. 27 grams of solid potassium nitrate ($KNO_3$) and then a solution of 68 grams of potassium nitrate in 200 ml of distilled water were added to the filtrate. The solution was left for eight hours with continuous stirring. A yellow-orange precipitate, a mixture of acid and potassium salts of the anion $PW_6V_6O_{40}^{-9}$ formed. The solids were filtered, washed, and recrystallized from a weakly acidic solution to form yellow and red crystals. A second batch of yellow crystals were obtained from the filtrate. Analysis of the second bath indicated anions of the form $PWV_{11}O_{40}^{-14}$ and $PWV_{12}O_{41}^{-11}$.

EXAMPLE XXIV

$Na_7PMo_8V_4O_{40}$

The preparation of this polyoxoanion is based on the preparation described in S. F. Davidson's Ph.D. Dissertation, University of Sheffield (1982). 5.7 grams of sodium phosphate dodecahydrate ($Na_3PO_4.12H_2O$), 17.25 grams of molybdenum trioxide ($MoO_3$) and 6.3 grams of vanadium pentoxide ($V_2O_5$) and 2.41 grams of $Na_2CO_3$ were dissolved in 75 ml of water. The solution was heated to 90° C. and kept there for one hour. The precipitate, $Na_7PMo_8V_4O_{40}$, was filtered, washed and dried. The filtrate was cooled and its volume reduced by a rotary evaporator to obtain a second batch of crystals.

EXAMPLE XXV

$Na_{12}P_2W_{12}V_6O_{62}$

See Example IVa, b, and c for the preparation of the sodium salt $Na_{12}H_6P_2W_{12}O_{50}$. 40 grams of the sodium salt were dissolved in 500 ml of 1M LiCl acidified to pH 2. A solution of 7.2 grams of sodium vanadate ($NaVO_3$) in 100 ml of water was added to the first solution, and the pH was adjusted to 5.5 with the addition of 1M HCl. A precipitate $Na_{12}P_2W_{12}V_6O_{62}$ was filtered, washed and dried. A second batch $K_{12}P_2W_{12}V_6O_{62}$ was obtained from the filtrate by the addition of potassium chloride.

EXAMPLE XXVI

$K_6H_3P_2W_{15}V_3O_{62}$ 50.0 grams of sodium vanadate ($NaVO_3$) were dissolved in 600 ml hot distilled water and then the solution was cooled to room temperature. The solution was acidified to pH 1.5 by the addition of 6.7 ml 12M HCl. The solution turned yellow. To the now vigorously stirred solution was slowly added 57.1 grams of $Na_{12}P_2W_{15}O_{56}.18H_2O$ (see Example Va), resulting in a cherry red solution. 3 ml of 12M HCl were added to alter pH to 1.5. Next, 45 grams of potassium chloride were added. A precipitate, $K_6H_3P_2W_{15}V_3O_{62}$, formed. It was filtered and recrystallized from water of pH 1.5, and then dried to give the final product.

In all the runs that are described in the following examples XXVII–XLII, the reaction vessel utilized was either (a) an 80 ml Fischer-Porter ® (Fischer-Porter Co., Warminster, Pa.) bottle having a magnetic stirrer capable of 250 rpm (hereinafter referred to as R1), (b) an 80 ml Fischer-Porter ® bottle with a motor driven titanium paddle stirrer (1750 rpm) (hereinafter referred to as R2), or (c) a 100 ml Fluitron SS316 reactor (5000 psi rating) with a conventional stirrer (2500 rpm maximum) (hereinafter referred to as R3). The observed relative oxidation rates, because of increased mass transport of oxygen and (or) olefin, increase from 1 to 4–6 to 20–40 in going from R1 to R2 to R3.

R1's were fitted with a pressure gage, oxygen inlet line, vent line, and a liquid injection port through which liquid (e.g., olefin) could be injected at any desired operating temperature and pressure. Each R1 used a 3" long, 1½" diameter Teflon ® (DuPont Co., Wilmington, Del.) coated stirring bar. The oxygen lines to the reactors were fitted with filters and check valves. The R1's were heated in a glycol bath whose temperature was controlled by a $I^2R$ Thermo-Watch. Each bath was protected from inadvertent overheating by an $I^2R$ Over-Temp Probe.

R2's were outfitted in a similar fashion as the R1's, the major difference being the mode of stirring, i.e., the motor driven two blade paddle stirrer. Both the stirrer shaft and paddle were made of titanium so that comparison runs using corrosive concentrations of chloride could be carried out.

R3 was a 100 ml reactor manufactured by Fluitron Inc. of Warminster, Pa. The double disk six pitched blade stirrer was originally designed to circulate the catalyst solution out of and into the reactor so that the reactor need not be depressurized for sampling. R3 was heated by an electrical heater. The temperature was monitored by a thermocouple. The temperature was set using a RI Instruments controller and was monitored on an Analog Devices Digital Thermometer. A Watlow over-heat monitor was used to shut off the whole system. Representative samples could be taken using a pressure syringe while R3 was in full operation.

All reactors were first loaded with the solvent followed by addition of the various catalyst components. The reactor was sealed and pressurized/depressurized at least four times with oxygen. The final pressure was left at 80 psig. The reactor was then heated to the reaction temperature. The olefin was injected using a pressure syringe without the need for depressurizing. Oxygen could be supplied by repressurizing as the pressure fell or by leaving the oxygen supply line open to a constant pressure source of the gas.

In R1 and R2 oxidation runs, uniform samples could not be obtained during a run. In R3 reactions, uniform samples could be obtained as a function of time.

After the desired reaction time, the reactors were quenched to room temperature and were depressurized. Injection of the water phase on a gas chromatograph column showed whether some very polar compounds had formed, e.g., acids. The reaction was then neutralized, extracted with methylene chloride, and the methylene chloride solution was also analyzed by GC.

In the following examples, "conversion" is defined as the moles of olefin reacted per mole of olefin fed; "selectivity" is defined as the moles of ketone produced per mole of olefin reacted; "yield" is defined as the product of selectivity and conversion; and "turnover per Pol" is defined as the moles of ketone produced per mole of Pd present in the system.

EXAMPLE XXVII

A series of 1-hexene oxidations were carried out in the presence of 15 ml distilled water, 1.5 ml 1N $H_2SO_4$, 625 mg of a polyoxoanion and 1:5 molar ratio of Pd(CF$_3$COO)$_2$:polyoxoanion. An identical series of comparison oxidations were done having a 1:5:10 molar ratio of Pd(CF$_3$COO)$_2$:polyoxoanion:CuSO$_4$2H$_2$O. All reactions were carried out with 2 ml of olefin in R1 according to the above-described general procedure. The reaction conditions were 85° C. and 80 psig O$_2$ for 8 hours. The results are compiled in Table 1.

of the olefin in R1 according to the general procedure. The reaction conditions were 85° C. and 80 psig O$_2$ for 8 hours. The results are compiled in Table 2.

These runs demonstrate that oxidations using isopolyoxoanions and a redox active metal give high conversions of olefin, with high selectivity to product, with highest observed turnovers on palladium.

TABLE 2

| Polyoxoanion | Pd(CF$_3$COO)$_2$ [mol] × 10$^3$ | Polyoxoanion [mol] × 10$^2$ | CuSO$_4$ [mol] × 10$^2$ | Hexene Conversion mol % | Selectivity to 2 Hexanone mol % | Turnovers per Pd |
|---|---|---|---|---|---|---|
| [Mo$_4$V$_8$O$_{36}$]$^{-8}$ | 2.79 | 1.39 | 2.79 | 47.4 | 89.7 | 150 |
| [Mo$_8$V$_4$O$_{36}$]$^{-4}$ | 2.79 | 1.39 | 2.79 | 76.0 | 86.8 | 222 |
| [W$_2$Mo$_6$V$_4$O$_{36}$]$^{-4}$ | 2.79 | 1.39 | 2.79 | 72.8 | 85.2 | 209 |
| [W$_6$Mo$_2$V$_4$O$_{36}$]$^{-4}$ | 2.79 | 1.39 | 2.79 | 43.4 | 84.7 | 126 |
| [W$_6$V$_6$O$_{36}$]$^{-6}$ | 2.79 | 1.39 | 2.79 | 58.7 | 90.2 | 179 |

EXAMPLE XXIX

A series of 1-hexene oxidations were carried out in the presence of 7.5 ml distilled water, 7.5 ml CH$_3$CN, 1.5 ml 1N H$_2$SO$_4$, 625 mg of P$_2$W$_{12}$Mo$_6$O$_{62}$$^{-6}$, 1:5 molar ratio of Pd(CF$_3$COO)$_2$:polyoxoanion, and a redox active metal. All reactions were carried out using R1 and 2 ml of olefin according to the general procedure.

The reaction conditions were 85° C. and 80 psig O$_2$ for 8 hours. The results are compiled in Table 3.

These runs demonstrate that there exist a number of redox active metals which lead to increased oxidation rates, selectivities, and turnovers per palladium.

TABLE 3

| Redox Active Metal (s) | Redox Active Metal(s) [mol] × 10$^2$ | Pd(CF$_3$COO)$_2$ [mol] × 10$^3$ | Polyoxoanion [mol] × 10$^3$ | Hexene Conversion mol % | Selectivity to 2-Hexanone mol % | Turnovers per Pd |
|---|---|---|---|---|---|---|
| — | — | 1.60 | 8.0 | 25.9 | 18.1 | 28 |
| CoSO$_4$ | 1.60 | 1.60 | 8.0 | 21.7 | 18.0 | 23 |
| MnSO$_4$ | 1.60 | 1.60 | 8.0 | 26.5 | 28.7 | 45 |
| FeSO$_4$ | 1.67 | 1.60 | 8.0 | 91.8 | 24.1 | 132 |
| CuSO$_4$ | 1.60 | 1.60 | 8.0 | 97.5 | 30.0 | 173 |

These runs demonstrate that the addition of a redox active metal can improve conversion and (or) selectivity.

EXAMPLE XXX

A series of 1-hexene oxidations were carried out in

TABLE 1

| Polyoxoanion | Pd(CF$_3$COO)$_2$ [mol]* × 10$^3$ | Polyoxoanion [mol] × 10$^2$ | CuSO$_4$ [mol] × 10$^2$ | Hexene Conversion mol % | Selectivity to 2-Hexanone mol % | Turnovers per Pd |
|---|---|---|---|---|---|---|
| P$_2$W$_{15}$V$_3$O$_{62}$$^{-9}$ | 1.60 | 0.80 | — | 30.8 | 76.9 | 143 |
| " | 1.60 | 0.80 | 1.58 | 35.9 | 99.1 | 214 |
| PMo$_6$V$_6$O$_{40}$$^{-9}$ | 3.54 | 1.77 | — | 53.7 | 90.8 | 131 |
| " | 3.54 | 1.77 | 3.53 | 73.7 | 95.0 | 189 |
| P$_2$W$_{12}$Mo$_6$O$_{62}$$^{-6}$ | 1.60 | 0.80 | — | 3.9 | 35.5 | 8 |
| " | 1.60 | 0.80 | 1.60 | 10.6 | 60.5 | 38 |
| Mo$_6$V$_6$O$_{36}$$^{-6}$ | 3.66 | 1.83 | — | 70.0 | 94.5 | 198 |
| " | 3.66 | 1.83 | 3.67 | 85.5 | 90.0 | 172 |
| Mo$_4$V$_8$O$_{36}$$^{-8}$ | 2.79 | 1.39 | — | 25.6 | 86.0 | 77 |
| " | 2.79 | 1.39 | 2.79 | 47.4 | 89.7 | 150 |
| W$_6$Mo$_2$V$_4$$^{-4}$ | 2.79 | 1.39 | — | 14.0 | 72.8 | 36 |
| " | 2.79 | 1.39 | 2.79 | 43.4 | 84.7 | 126 |

*[mol] represents mole per liter.

EXAMPLE XXVIII

A series of 1-hexene oxidations were carried out in the presence of 16.5 mls of aqueous solution adjusted to pH 1.6 with concentrated sulfuric acid. The solutions had a 1:5:10 molar ratio of Pd(CF$_3$COO)$_2$:POA:CuSO$_4$5H$_2$O. The reactions were carried out with 2 ml the presence of 15 ml distilled water, 1.5 ml 1N H$_2$SO$_4$, 625 mg of polyoxoanion, and 1:5 molar ratio of Pd(CF$_3$COO)$_2$:polyoxoanion. An identical series of comparison oxidations were done in the presence of 7.5 ml distilled water, 7.5 ml acetonitrile (CH$_3$CN), and 1.5 ml 1N H$_2$SO$_4$. All reactions were carried out with 2 ml of olefin in R1 according to the general procedure. The reaction conditions were 85° C. and 80 psig $O_2$ for 8 hours. The results are compiled in Table 4.

These runs demonstrate that the addition of a ligand, in this case acetonitrile, can improve conversion and oxidation turnovers per palladium atom. Selectivities in this example are lower as a result of the higher conversions attained.

TABLE 4

| Polyoxoanion | Pd(CF$_3$COO)$_2$ [mol] × 10$^3$ | Polyoxoanion [mol] × 10$^2$ | CH$_3$CN + or − | Hexene Conversion mol % | Selectivity to 2-Hexanone mol % | Turnovers per Pd |
|---|---|---|---|---|---|---|
| P$_2$Mo$_{18}$O$_{62}$$^{-6}$ | 2.13 | 1.07 | − | 17.5 | 48.6 | 38 |
| " | 2.13 | 1.07 | + | 48.5 | 43.8 | 95 |
| PW$_6$V$_6$O$_{40}$$^{-9}$ | 2.77 | 1.39 | − | 55.2 | 91.6 | 174 |
| " | 2.77 | 1.39 | + | 95.9 | 71.5 | 236 |
| P$_2$W$_{12}$Mo$_6$O$_{62}$$^{-6}$ | 1.60 | 0.80 | − | 5.2 | 29.3 | 9 |
| " | 1.60 | 0.80 | + | 25.9 | 18.1 | 28 |

EXAMPLE XXXI

A series of 1-hexane oxidations were carried out in the presence of 15 ml distilled water, 1.5 ml 1N H$_2$SO$_4$, 625 mg of polyoxoanion, and 1:5 molar ration of Pd(CF$_3$COO)$_2$:polyoxoanion. An identical series of comparison oxidations were done having a 1:5:10 molar ratio of Pd(CF$_3$COO)$_2$:polyoxoanion:CuSO$_4$.5H$_2$O in the presence of 7.5 ml distilled water 7.5 ml CH$_3$CN, and 1.5 ml 1N H$_2$SO$_4$. All reactions were carried out with 2 ml of olefin in R1's according to the general procedure. The reaction conditions were 85° C. and 80 psig $O_2$ for 8 hours. The results are compiled in Table 5.

These runs demonstrate that the addition of a redox active metal and a ligand can in most cases improve both conversion and selectivity. In all cases, one sees an increase in the number of molecules of ketone produced per palladium atom present.

EXAMPLE XXXII

A series of 1-hexene oxidations were carried out using a 1:5 molar ratio of Pd(CF$_3$COO)$_2$:polyoxoanion. Reactions were run in the absence of a redox active metal and a ligand and then compared to those in the presence of a redox active metal and (or) ligand. The ratios of solvents:ligands:redox active metals were identical to those in Examples XXVII to XXXI. All reactions were carried out at 85° C. and 80 psig $O_2$ for 8 hours. The results are compiled in Table 6.

These oxidations demonstrate that the addition of a redox active metal and a ligand can increase conversion and selectivity. It is further demonstrated that, as expected from the theory, the effects of the redox active metal and ligand are not merely additive. In the case of PMo$_6$W$_6$O$_{40}$$^{-3}$, the additive turnovers per palladium would be 9. The observed effect of both the addition of Cu$^{+2}$ and CH$_3$CN is 145.

TABLE 6

| Polyoxoanion | Pd(CF$_3$COO)$_2$ [mol] × 10$^3$ | Polyoxoanion [mol] × 10$^2$ | CuSO$_4$ [mol] × 10$^2$ | CH$_3$CN + or − | Hexene Conversion mol % | Selectivity to 2-Hexanone mol % | Turnovers per Pd |
|---|---|---|---|---|---|---|---|
| PMo$_6$W$_6$O$_{40}$$^{-3}$ | 2.53 | 1.27 | — | − | 4.2 | 9.1 | 1 |
| " | 2.53 | 1.27 | 2.54 | − | 3.6 | 20.7 | 2 |
| " | 2.53 | 1.27 | — | + | 24.0 | 7.7 | 7 |
| " | 2.53 | 1.27 | 2.54 | + | 99.4 | 38.6 | 145 |
| P$_2$W$_{12}$Mo$_6$O$_{62}$$^{-6}$ | 1.60 | 0.80 | — | − | 5.2 | 29.3 | 9 |
| " | 1.60 | 0.80 | 1.60 | − | 10.6 | 60.5 | 38 |
| " | 1.60 | 0.80 | — | + | 25.9 | 18.1 | 28 |
| " | 1.60 | 0.80 | 1.60 | + | 97.5 | 30.0 | 136 |
| P$_2$Mo$_{18}$O$_{62}$$^{-6}$ | 2.13 | 1.07 | — | − | 17.5 | 48.6 | 38 |
| " | 2.13 | 1.07 | 2.14 | − | 34.6 | 33.2 | 51 |
| " | 2.13 | 1.07 | — | + | 48.5 | 43.8 | 95 |
| " | 2.13 | 1.07 | 2.14 | + | 86.4 | 23.1 | 89 |

EXAMPLE XXXIII

A series of 1-hexene oxidations were carried out in the presence and absence of the additives of the instant invention. The comparison reactions were carried out at high stirring rates in R3 according to the general procedure. The reaction conditions were 85° C., 100 psig of oxygen, and pH 1.5. The volumes of solution and

TABLE 5

| Polyoxoanion | Pd(CF$_3$COO)$_2$ [mol] × 10$^3$ | Polyoxoanion [mol] × 10$^2$ | CuSO$_4$ [mol] × 10$^2$ | CH$_3$CN + or − | Hexene Conversion mol % | Selectivity to 2-Hexanone mol % | Turnovers per Pd |
|---|---|---|---|---|---|---|---|
| PMo$_6$W$_6$O$_{40}$$^{-3}$ | 2.53 | 1.27 | — | − | 4.2 | 9.1 | 1 |
| " | 2.53 | 1.27 | 2.54 | + | 99.4 | 38.6 | 145 |
| P$_2$W$_{12}$Mo$_6$O$_{62}$$^{-6}$ | 1.60 | 0.80 | — | − | 5.2 | 29.3 | 9 |
| " | 1.60 | 0,80 | 1.60 | + | 97.5 | 30.0 | 136 |
| P$_2$Mo$_{18}$O$_{62}$$^{-6}$ | 2.13 | 1.07 | — | − | 17.5 | 48.6 | 38 |
| " | 2.13 | 1.07 | 2.14 | + | 86.4 | 23.1 | 89 |
| P$_2$W$_{12}$Mo$_5$VO$_{62}$$^{-7}$ | 1.57 | 0.78 | — | − | 4.8 | 19.7 | 6 |
| " | 1.57 | 0.78 | 1.56 | + | 12.2 | 31.3 | 23 |
| Mo$_6$V$_6$O$_{36}$$^{-6}$ | 3.66 | 1.83 | — | − | 85.5 | 90.0 | 172 |
| " | 3.66 | 1.83 | 3.67 | + | 99.6 | 75.2 | 195 | olefin were 39 mll and 2 ml respectively. The catalyst components and their concentrations are listed in Table 7, together with the results.

These runs demonstrate that the addition of a redox active metal and (or) ligand can improve conversion and (or) selectivity under industrially acceptable process conditions.

TABLE 7

| Polyoxoanion | Polyoxoanion [mol] × $10^2$ | Pd(NO$_3$)$_2$ [mol] × $10^3$ | Cu(NO$_3$)$_2$ [mol] × $10^2$ | CH$_3$CN % | Time min. | Conversion of 1-Hexene mol % | Selectivity to 2-Hexanone mol % |
|---|---|---|---|---|---|---|---|
| PW$_6$Mo$_6$O$_{40}$$^{-3}$ | 1.03 | 2.06 | — | — | 20 | 21.4 | 58.2 |
| " | 1.03 | 2.06 | 2.07 | — | 19 | 39.2 | 60.4 |
| PW$_6$V$_6$O$_{40}$$^{-9}$ | 1.03 | 2.06 | — | — | 56 | 91.7 | 85.8 |
| " | 1.03 | 2.06 | 2.07 | 25 | 21 | 92.5 | 87.6 |
| PMo$_6$V$_6$O$_{40}$$^{-9}$ | 2.59 | 5.18 | — | — | 89 | 96.5 | 81.3 |
| " | 2.59 | 5.18 | 10.4 | 40 | 16 | 96.4 | 87.0 |

EXAMPLE XXXIV 1-hexene was oxidized in the presence of 7.5 ml distilled water, 7.5 ml acetonitrile, 1.5 ml 1N H$_2$SO$_4$ and PW$_6$V$_6$O$_{40}$$^{-9}$. The oxidations were carried out with 2 ml of the olefin in R1 at 85° C. and 80 psig O$_2$ for 8 hours according to the general procedure. The amounts of the catalyst components and the results are shown in Table 8.

Table 8 also shows two 1-hexene oxidations in the presence of 15 ml distilled water, 1.5 ml 1N H$_2$SO$_4$ and PV$_{14}$O$_{42}$$^{-9}$. The reactions were carried out with 2 ml of the olefin in R2 at 85° C. and 80 psig O$_2$ for one hour.

These oxidations demonstrate that the product distribution, yield and selectivity are not a strong function of the palladium counterions, i.e., any one of a number of counterions can be used.

TABLE 8

| Reactor | Pd Salt Anion | Pd$^{+2}$ [mol] × $10^3$ | Polyoxoanion [mol] × $10^2$ | Hexene Conversion mol % | Selectivity to 2-Hexanone mol % | Turnovers per Pd per hr |
|---|---|---|---|---|---|---|
| R1 | SO$_4$$^{-2}$ | 2.77 | 1.39 | 36.4 | 45.1 | 7 |
| R1 | CH$_3$COO$^-$ | 2.77 | 1.39 | 35.0 | 51.1 | 8 |
| R1 | NO$_3$$^-$ | 2.77 | 1.39 | 35.9 | 45.0 | 7 |
| R2 | NO$_3$$^-$ | 3.56 | 1.78 | 34.0 | 97.0 | 77 |
| R2 | CF$_3$COO$^-$ | 3.56 | 1.78 | 33.0 | 99.7 | 73 |

EXAMPLE XXXV 1-hexene was oxidized by palladium nitrate in the presence of a redox active metal and (or) ligand but in the absence of a polyoxoanion. The amounts of solvent and catalyst components are shown in Table 9. The oxidations were carried out with 2 ml of the olefin and R1 according to the general procedure. The oxidation conditions were 85° C. and 80 psig O$_2$ for 8 hours. The results together with a comparison run containing polyoxoanions appear in Table 9.

These examples demonstrate that the palladium reoxidation requires a polyoxoanion component. In all of the comparison runs not containing a polyoxoanion, palladium metal dropped out of the reaction solution.

TABLE 9

| Water ml | CH$_3$CN ml | 1N H$_2$SO$_4$ ml | Pd(NO$_3$)$_2$ [mol] × $10^3$ | Cu(NO$_3$)$_2$ [mol] × $10^2$ | Polyoxoanion* [mol] × $10^2$ | Hexene Conversion mol % | Selectivity to 2-Hexanone mol % | Turnovers per Pd |
|---|---|---|---|---|---|---|---|---|
| 15.0 | — | 1.5 | 2.92 | — | — | 7.7 | 22.9 | 6 |
| 15.0 | — | 1.5 | 2.92 | 2.63 | — | 6.2 | 23.9 | 5 |
| 7.5 | 7.5 | 1.5 | 2.92 | — | — | 36.6 | 26.8 | 33 |
| 7.5 | 7.5 | 1.5 | 2.92 | 2.63 | — | 38.1 | 24.0 | 31 |
| 15.0 | — | 1.5 | 2.77 | 2.63 | 1.39 | 52.4 | 88.4 | 145** |

*[PW$_6$V$_6$O$_{40}$]$^{-9}$
**Compare to first run of Table 9 showing 6 turnovers/Pd.

EXAMPLE XXXVI 1-hexene was oxidized using tthe three different reactors R1, R2, and R3. The polyoxoanion used in this case was PV$_{14}$O$_{42}$$^{-9}$ prepared according to example XXI. All of the reactions were carried out according to the general procedure. Reactions in R1 and R2 were carried out in the presence of 15 ml distilled water, 1.5 ml 1N H$_2$SO$_4$, and 625 mg of PV$_{14}$O$_{42}$$^{-9}$. R3 had slightly different conditions with 37.3 ml of distilled water, 3.73 ml 1N H$_2$SO$_4$, and 713.8 mg PV$_{14}$O$_{42}$$^{-9}$. The palladium:polyoxoanion ratio in each case was 1:5, with R1 and R2 using Pd(CF$_3$COO)$_2$ and R3 using PdNO$_3$.3-H$_2$O. The oxidations were carried out with 2 ml olefin:16.5 ml solution at 85° C. and 80 psig O$_2$ for 480 minutes, 60 minutes and 27 minutes, respectively.

The fourth entry in Table 10 shows that, in this example, the reaction rate does not depend on the palladium counterion since it is identical to the second run except for using Pd(NO$_3$)$_2$.3H$_2$O instead of Pd(CF$_3$COO)$_2$.

These oxidations demonstrate that the oxidation rate increases significantly as one increases the reactant transport with higher stirring speeds and better reactor designs (R1→R2→R3). This also demonstrates that one can obtain very good selectivities at reasonable conversions (33% conversion, 99.7% selectivity) without large amounts of overoxidation.

TABLE 10

| Reactor | Time (min) | Hexene Conversion mol % | Selectivity to 2-Hexanone mol % | Turnovers per Pd per hr |
|---|---|---|---|---|
| R1 | 480 | 66.3 | 91.3 | 17 |
| R2 | 60 | 33.0 | 99.7 | 73 |
| R3 | 27 | 84.4 | 90.2 | 338 |
| *R2 | 60 | 34.0 | 97.0 | 77 |

*Uses Pd(NO$_3$)$_2$.3H$_2$O

EXAMPLE XXXVII 1-hexene was oxidized using the three different reactors R1, R2, and R3. The polyoxoanions used in this case where P$_2$W$_{12}$Mo$_6$O$_{62}^{-6}$ and PW$_6$V$_6$O$_4^{-9}$. The oxidations were carried out according to the general procedure. Reactions in R1 and R2 were carried out in the presence of 7.5 ml distilled water, 7.5 ml CH$_3$CN, 1.5 ml 1N H$_2$SO$_4$, 625 mg of polyoxoanion, and a 1:5 ratio of Pd(CF$_3$COO)$_2$:polyoxoanion. R3 had slightly different conditions with 29.3 ml distilled water, 9.7 ml CH$_3$CN, 1.704 g P$_2$W$_{12}$Mo$_6$O$_{62}^{-6}$, and a 1:5 ratio of Pd(NO$_3$)$_2$.3H$_2$O:polyoxoanion. The oxidations were carried out with 2 ml olefin:16.5 ml solution at 85° C. and 80 psig O$_2$, for 480 min, 60 min, and 30 min, respectively. The results appear in Table 11.

These oxidations demonstrate that the oxidation rate not only increases significantly with stirring rate but it can do so at the expense of isomerization which accounts for the better selectivity observed in R3 than in R1.

EXAMPLE XXXVIII 1-hexene was oxidized using the preferred catalyst systems of the best prior art in which halide ions are part of the catalyst system. These catalyst systems were tested in R2 at the process conditions of the instant invention, i.e. 85° C. and 80 psig O$_2$ for one hour. The catalyst preparations and the various concentrations of solvents and reagents were taken from the literature as indicated in Table 12. The oxidation results appear in the same table.

These examples demonstrate that the catalyst systems of the instant invention are superior to those described in the prior art.

TABLE 12

| Run # | Conversion of 1-Hexene mol % | Selectivity to 2-Hexanone mol % | Turnovers per Pd | Pd$^{+2}$ [mol] × 10$^3$ | Polyoxoanion [mol] × 10$^2$ | Co-Catalyst | Co-Catalyst [mol] × 10$^2$ |
|---|---|---|---|---|---|---|---|
| 1 | 10 | 80 | 6.7 | 9.6 | — | CuCl$_2$.2H$_2$O | 165.0 |
|   |    |    |     |     |   | Cu(OAc)$_2$.H$_2$O | 8.5 |
|   |    |    |     |     |   | HCl | 19.5 |
|   |    |    |     |     |   | CH$_3$COOH | 114.0 |
| 2 | 77 | 43 | 8.4 | 59.9$^6$ | 30.6$^6$ | CTMABr$^7$ | 1.2$^8$ |
| 3 | 37 | 70 | 114 | 2.08 | 20 | — | — |
| 4 | 98 | 18 | 39.8 | 4.19 | — | Fe$_2$(SO$_4$)$_3$.9H$_2$O$^9$ | 50.0 |
|   |    |    |     |     |   | HCl | 5.0 |
| 5 | 25 | 96 | 79.1 | 2.77 | 1.39 | CuSO$_4$.5H$_2$O | 2.6 |

[1] Standard Wacker used in oxidation of ethylene to acetaldehyde. Stanford Research Institute P.E.P. Report No. 24A2, Dec. 1976.
[2] U.S. Pat. No. 4,434,082, Example 9
[3] British Patent 1,508,331, Example 6.
[4] British Patent 1,240,889, Example 1-run 4.
[5] Instant Invention using PW$_6$V$_6$O$_{40}^{-9}$
[6] Concentration in aqueous phase.
[7] CTMABr = cetyltrimethyl ammonium bromide.
[8] Concentration using the total volume of solution (2 phases = 28.3 ml)
[9] 79.4% Fe$_2$(SO$_4$)$_3$

EXAMPLE XXXIX 1-hexene oxidations were carried out in R3. The previously reported best polyoxoanion system involved PMo$_6$V$_6$O$_{40}^{-9}$/Pd$^{+2}$. As a result, this system was compared with an identical catalyst system of the instant invention except for the addition of a ligand (CH$_3$CN) and a redox active metal (Cu$^{+2}$). Both reactions were run according to the general procedure in a 40 ml volume using 2 ml 1-hexene, 85° C. and 85 psig O$_2$. In the case of the instant invention 33% of the volume was acetonitrile. The concentration of the various catalyst components and the results appear in Table 13. The oxidation to 2-hexanone is 5 times faster with the additives of the instant invention. The yield of the desired product is higher at high conversions.

These runs demonstrate that the addition of a ligand and a redox active metal can increase significantly the rate of reaction and selectity obtained by the prior art.

TABLE 11

| Polyoxoanion | Reactor | Time (min) | Hexene Conversion mol % | Selectivity to 2-Hexanone mol % | Turnovers per Pd per hr |
|---|---|---|---|---|---|
| P$_2$W$_{12}$Mo$_6$O$_{62}^{-6}$ | R1 | 480 | 97.5 | 30.0 | 22 |
| " | R2 | 60 | 85.0 | 23.0 | 110 |
| " | R3 | 30 | 97.5 | 89.7 | 349 |
| PW$_6$V$_6$O$_{40}^{-9}$ | R1 | 480 | 38.9 | 53.7 | 9 |
| " | R2 | 60 | 36.0 | 56.9 | 72 |
| " | R3 | 21 | 92.5 | 87.6 | 426 |

TABLE 13

| Run # | Polyoxoanion | Polyoxoanion mol × 10² | Pd(NO₃)₂ [mol] × 10³ | Cu(No₃)₂ [mol] × 10 | CH₃CN % |
|---|---|---|---|---|---|
| 1 | PMo₆V₆O₄₀⁻⁹ | 2.59 | 5.18 | 0 | 0 |
| 2 | PMo₆V₆O₄₀⁻⁹ | 2.59 | 5.18 | 1.04 | 33 |
|  | Time (min) | 16.0 | 48.0 | 89.0 | 142.0 |
| 1 | Conversion mol % | 81.6 | 91.4 | 96.5 | 99.1 |
| 1 | Selectivity mol % | 91 | 84.3 | 81.3 | 75.5 |
| 1 | % Yield of 2-Hexanone | 74.3 | 77.1 | 78.5 | 74.8 |
| 2 | Conversion mol % | 96.4 | 99.0 | — | 99.8 |
| 2 | Selectivity mol % | 87.0 | 87.7 | — | 80.9 |
| 2 | % Yield of 2-Hexanone | 83.9 | 86.8 | — | 80.7 |

EXAMPLE XL

In order to compare the rates of oxidation of different olefins, and their selectivities toward the corresponding carbonyl compound, ethylene, 1-butene, 4-methyl 1-pentene, cyclohexene, 1-octene and trans 2-octene were individually oxidized in R3 under identical conditions. The polyoxoanion used in these oxidations was $PMo_6V_6O_{40}^{-9}$ prepared according to example I. All of the reactions were carried out according to the general procedure. The reaction conditions were 85° C., 100 psig total pressure and 2000 RPM without baffles. The solvent system consisted of 29.25 ml of water, 9.75 ml of acetonitrile and a few drops of 36N $H_2SO_4$, enough to guarantee pH 1.5 after addition of the catalyst. The catalyst system consisted of 1.25 g of $K_5H_4PMo_6V_6O_{40}.10H_2O$, 0.0589 g of $Pd(NO_3)_2.3H_2O$ and 0.9631 g of $Cu(NO_3)_2.H_2O$. Each olefin was added at reaction temperature in amounts of 2 ml. Table 14 summarizes the results.

These results demonstrate that under conditions of the instant invention, high initial rates and selectivities are achieved for a variety of olefins. FIG. 1 shows that the decrease in relative rates of oxidation of ⓡ-olefins with increasing carbon number is much less dramatic than in prior art systems, rendering commercial oxidation of higher olefins economically attractive. In FIG. 1, curve b represents published information of the relative rates of oxidation of the various olefins by the Wacker system (Smidt et al., Angew. Chem., Vol. 71, No. 4, 1959 and Smidt et al., Proc. 6th World Petr. Congress, Section IV, Paper 40-PD9, Frankfurt/Main, June 19–26, 1963). Curve a represents the initial rate of oxidation of the various olefins (see Table 14) relative to the initial rate of ethylene oxidation, per mole equivalent of olefin in the feed to account for the proportionality of the oxidation rate with the olefin concentration. Point A in this Figure is equivalent to an oxidation rate of $8.58 \times 10^{-7}$ moles $C_2H_4$/sec ml for the present invention at 85° C., $8.21 \times 10^{-7}$ moles $C_2H_4$/sec ml for commercial Wacker oxidation of ethylene at 110° C. (SRI PEP Report 24A2, "Ethylene to Acetaldehyde", December 1976), and only $9.68 \times 10^{-8}$ moles $C_2H_4$/sec ml for Belgian Pat. No. 828,603 (Example 1) at 90° C. These latter numbers demonstrate that much higher rates are achieved under the conditions of the present invention.

TABLE 14

| Olefin | Initial Rate of Olefin Disappearance moles olefin converted sec. cc solution | Initial Rate of Carbonyl compound Formation moles carbonyl formed sec. cc solution | Initial Rate Selectivity moles carbonyl formed moles olefin converted | Run Time min | Olefin Conversion At End of Run moles olefin converted moles olefin fed (%) |
|---|---|---|---|---|---|
| $C_2H_4$ | $8.58 \times 10^{-7}$ | $7.10 \times 10^{-7}$ | 82.7 | 60 | 100.0 |
| 1-butene | $7.57 \times 10^{-7}$ | $6.84 \times 10^{-7}$ | 90.3 | 172 | 89.9 |
| 4-methyl-1-pentene | $2.43 \times 10^{-7}$ | $1.92 \times 10^{-7}$ | 79.0 | 258 | 80.0 |
| cyclohexene | $3.23 \times 10^{-7}$ | $3.15 \times 10^{-7}$ | 97.5 | 142 | 91.9 |
| 1-pentene | $4.58 \times 10^{-7}$ | $4.16 \times 10^{-7}$* | 90.8 | 142 | 99.8 |
| 1-octene | $2.86 \times 10^{-7}$ | $1.87 \times 10^{-7}$ | 65.4 | 141 | 85.9 |
| trans-2-octene | $1.57 \times 10^{-7}$ | $1.37 \times 10^{-7}$* | 89.5 | 278 | 84.2 |

*2-ketone + 3-ketone

EXAMPLE XLI

In order to compare the rates of oxidation of different olefins, and their selectivities toward the corresponding carbonyl compound, 1-butene, cis 2-butene and trans 2-butene were individually oxidized in R3 under identical conditions. The polyoxoanion used in these oxidations was $PV_{14}O_{42}^{-9}$ prepared according to example XXI. All of the reactions were run according to the general procedure. The reactions were carried out at 85° C. 100 psig total pressure and 2000 rpm. The solvent system consisted of 30.0 ml distilled water, 10 ml acetonitrile and a few drops of 36N $H_2SO_4$, enough to guarantee a pH of 1.5 after addition of the catalyst. The catalyst system consisted of 1.1526 grams of $Na_8HPV_{14}O_{42}.10H_2O$, 0.0589 grams of $Pd(NO_3)_2.3H_2O$ and 0.631 gram of $Cu(NO_3)_2.2\frac{1}{2}H_2O$. Each olefin was added at reaction temperature in amounts of 1 ml. Table 15 summarizes the results.

These results demonstrate that under conditions of the instant invention 2-butene isomers react at least as fast as 1-butene, with high selectivity of MEK and high conversions. This again shows the superiority of the present invention over the conventional Wacker system, where the relative oxidation rates of the butenes was found to be: (1-Butene):(trans 2-butene+cis 2-butene)=1:0.29. (Smidt et al., Proc. 6th World Petr. Congr., Section IV, Paper 40-PD9, Frankfurt/Main, June 19–26, 1963.)

EXAMPLE XLIII

The corrosion testing of stainless steel 316 was carried out according to NACE Standard TM.01.69 (1976 Revision).

The corrosion studies were done in a 500 ml resin flask which was provided with: reflux condenser, trap, oxygen sparger, thermowell, heating mantle, temperature regulator, variable speed motor and a glass specimen support system.

The SS316 coupons ($3'' \times \frac{3}{4}'' \times \frac{1}{8}''$) were submerged in the reaction solution and olefin oxidation was carried out at 85° C. and atmospheric $O_2$ pressure.

Corrosion rates are expressed as millimeter penetration per year (mmpy) and were calculated as follows:

$$mmpy = \frac{(\text{weight loss}) \times 87.6}{(\text{area})(\text{time})(\text{metal density})}$$

where weight loss is in milligrams, area is $cm^2$ of metal surface exposed, time is in hours, and density in $gm/cm^3$.

Figure 2:
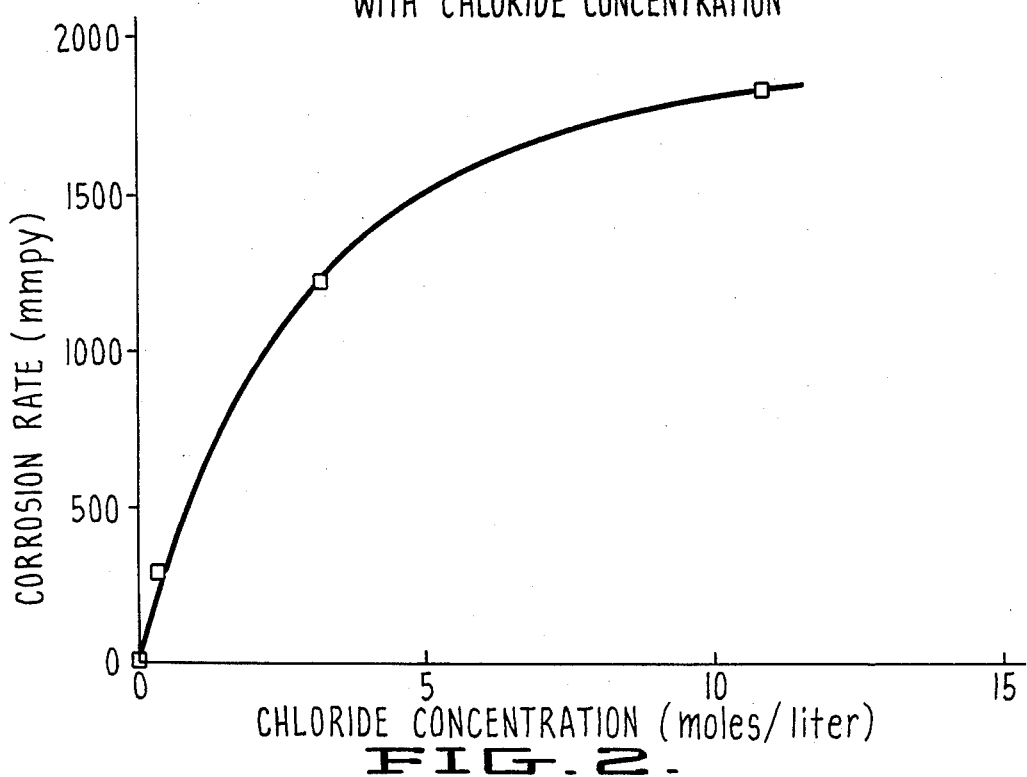
FIG. 2 is a plot of SS316 corrosion rates versus chloride concentration.

Table 17 shows three $PdCl_2/CuCl_2$ Wacker systems at various chloride levels and their corrosion rates after two hours run time. Entry 1 is a system of the instant invention with a small amount of chloride. No corrosion was observed in the latter system and enormous amounts of corrosion were observed in the $PdCl_2/CuCl_2$ systems. FIG. 2 shows a plot of the corrosion rate versus chloride ($Cl^-$) concentration.

These corrosion tests demonstrate that chloride-free polyoxoanion systems, or those polyoxoanion systems with only trace chloride contamination, show no corrosion of SS 316. Thus, the systems of the instant invention can use cheaper materials of construction.

TABLE 15

| Olefin | Initial Rate of Olefin Disappearance moles olefin converted sec. cc solution | Initial Rate of MEK Formation moles MEK* formed sec. cc solution | Initial Rate Selectivity moles MEK* formed moles olefin converted | Run Time min | Olefin Conversion At End of Run moles olefin converted moles olefin fed (%) |
|---|---|---|---|---|---|
| 1-Butene | $1.37 \times 10^{-7}$ | $1.27 \times 10^{-7}$ | 92.2 | 201 | 90.2 |
| Trans 2-Butene | $1.65 \times 10^{-7}$ | $1.60 \times 10^{-7}$ | 96.7 | 261 | 95.7 |
| Cis 2-Butene | $1.59 \times 10^{-7}$ | $1.31 \times 10^{-7}$ | 82.4 | 289 | 99.9 |

*MEK = methyl ethyl ketone

EXAMPLE XLII

Cyclohexene was oxidized to cyclohexanone in the presence of 15 ml distilled water, 15 ml acetonitrile, 3 ml 1N $H_2SO_4$, $PMo_6V_6O_{40}^{-9}$, and in the presence or absence of copper ions. The oxidations were carried out in R1 according to the general procedure. The oxidations were done with 5 ml olefin at 75° C. and 80 psig $O_2$ for 4 hours. The results appear in Table 16.

These examples demonstrate that the addition of copper ions significantly reduces dehydrogenation, allylic oxidation and diol formation.

TABLE 17

| Oxidation System | $Cl^-$ moles/liter | Corrosion Rate (mmpy) |
|---|---|---|
| $PMo_6V_6O_{40}^{-6}$ | 0.004 | 0 |
| Wacker 1 | 0.35 | 293 |
| Wacker 2* | 3.17 | 1223 |

TABLE 16

| $Cu(NO_3)_2$ [mol] $\times 10^2$ | $Pd(NO_3)_2$ [mol] $\times 10^3$ | $PMo_6V_6O_{40}^{-9}$ [mol] $\times 10^2$ | benzene mol % | cyclohexanone mol % | cyclohexenone mol % | cyclohexenol OH mol % | trans cyclohexanediol mol % | Conversion of cyclohexene mol % |
|---|---|---|---|---|---|---|---|---|
| — | 4.00 | 2.00 | .08 | 20.2 | 7.4 | .74 | 1.16 | 33.5 |
| 4.5 | 4.00 | 2.00 | .05 | 35.6 | 2.58 | .25 | .38 | 41.0 |

TABLE 17-continued

| Oxidation System | Cl⁻ moles/liter | Corrosion Rate (mmpy) |
|---|---|---|
| Wacker 3 | 10.87 | 1825 |

*Identical to system used commercially for oxidizing ethylene to acetaldehyde.

It will be apparent to one skilled in the art that the use of additional materials in the reaction mixtures such as other oxidizing agents and organic solvents, provided that these do not substantially adversely affect the reactions, is not precluded.

We claim:

1. A catalyst system useful for olefin oxidation to a carbonyl product which comprises:
   (a) at least one polyoxoanion component which is a member selected from the group consisting of compounds which have the general formula:

$[X_xM_aM'_bM''_cO_z]^{-m}$ wherein
   X is a member selected from the group consisting of B, Si, Ge, P, As, Se, Te, I, Co, Mn and Cu;
   M, M' and M'' are members independently selected from the group consisting of W, Mo, V, Nb, Ta and Re;
   x is zero for isopolyoxoanions and mixed isopolyoxoanions;
   x is an integer greater than zero for heteropolyoxoanions;
   a, z and m are integers greater than zero;
   b, c are integers; and
   $a+b+c \geq 2$;
   (b) at least one palladium component; and
   (c) at least one nitrile ligand.

2. The catalyst system of claim 1 wherein the ligand is acetonitrile.

3. An unsupported, aqueous catalyst system useful for olefin oxidation to a carbonyl product which comprises:
   (a) at least one polyoxoanion component which is a member selected from the group consisting of compounds which have the general formula:

$[X_xM_aM'_bM''_cO_z]^{-m}$ wherein
   X is a member selected from the group consisting of B, Si, Ge, P, As, Se, Te, I, Co, Mn and Cu;
   M, M' and M'' are members independently selected from the group consisting of W, Mo, V, Nb, Ta and Re;
   x is zero for isopolyoxoanions and mixed isopolyoxoanions;
   x is an integer greater than zero for heteropolyoxoanions;
   a, z and m are integers greater than zero;
   b, c are integers; and
   $a+b+c \geq 2$;
   (b) at least one palladium component; and
   (c) at least one redox active metal component wherein said catalyst system is substantially free of nitrogen compounds selected from the group consisting of nitric acid, nitrogen oxides and esters of nitrous acid.

4. The catalyst system of claim 3 wherein said redox active metal component is a member selected from the group consisting of CuSO₄, Cu(CH₃COO)₂ and Cu(NO₃)₂.

5. The catalyst system of claim 3 wherein said redox active metal component is a member selected from the group consisting of Fe(CH₃COO)₂, FeSO₄ and MnSO₄.

6. An unsupported aqueous catalyst system useful for olefin oxidation to a carbonyl product which comprises:
   (a) at least one polyoxoanion component which is a member selected from the group consisting of compounds which have the general formula:

$[X_xM_aM'_bM''_cO_z]^{-m}$ wherein
   X is a member selected from the group consisting of B, Si, Ge, P, As, Se, Te, I, Co, Mn and Cu;
   M, M' and M'' are members independently selected from the group consisting of W, Mo, V, Nb, Ta and Re;
   x is zero for isopolyoxoanions and mixed isopolyoxoanions;
   x is an integer greater than zero for heteropolyoxoanions;
   a, z and m are integers greater than zero;
   b, c are integers; and
   $a+b+c \geq 2$;
   (b) at least one palladium component; and
   (c) at least one redox active metal component, wherein said redox active metal component is provided separate and distinct from said polyoxoanion component.

7. The catalyst system of claim 6 wherein said redox active metal component is a member selected from the group consisting of CuSO₄, Cu(CH₃COO)₂ and Cu(NO₃)₂.

8. The catalyst system of claim 6 wherein said redox active metal component is selected from the group consisting of Fe(CH₃COO)₂, FeSO₄ and MnSO₄.

9. The catalyst system of claim 6 wherein said redox active metal is selected from the group consisting of copper salts.

10. The catalyst system of claim 6 wherein said redox active metal is selected from the group consisting of iron salts.

11. The catalyst system of claim 6 wherein said redox active metal is selected from the group consisting of manganese salts.

12. A catalyst system useful for olefin oxidation to a carbonyl product which comprises:
    (a) at least one polyoxoanion component which is a member selected from the group consisting of compounds which have the general formula:

$[X_xM_aM'_bM''_cO_z]^{-m}$ wherein
    X is a member selected from the group consisting of B, Si, Ge, P, As, Se, Te, I, Co, Mn and Cu;
    M, M' and M'' are members independently selected from the group consisting of W, Mo, V, Nb, Ta and Re;
    x is zero for isopolyoxoanions and mixed iosopolyoxoanions;
    x is an integer greater than zero for heteropolyoxoanions;
    a, z and m are integers greater than zero;
    b, c are integers; and
    $a+b+c \geq 2$;
    (b) at least one palladium component;
    (c) at least one redox active metal component; and, (d) at least one nitrile ligand.

13. The catalyst system of claim 12 wherein said redox active metal component is a member selected from the group consisting of $CuSO_4$, $Cu(CH_3COO)_2$ and $Cu(NO_3)_2$.

14. The catalyst system of claim 12 wherein said redox active metal component is a member selected from the group consisting of $Fe(CH_3COO)_2$, $FeSO_4$ and $MnSO_4$.

15. The catalyst system of claim 12 wherein the ligand is acetonitrile.

16. The catalyst system of claim 12 wherein said redox active metal is selected from the group consisting of copper salts.

17. The catalyst system of claim 12 wherein said redox active metal is selected from the group consisting of iron salts.

18. The catalyst system of claim 12 wherein said redox active metal is selected from the group consisting of manganese salts.

19. An unsupported, aqueous catalyst system useful in olefin oxidation to a carbonyl compound which comprises:
(a) at least one molybdenum-free polyoxoanion component; and,
(b) at least one palladium component wherein said catalyst system is substantially free of nitrogen compounds selected from the group consisting of nitric acid, nitrogen oxides and esters of nitrous acid.

20. An unsupported, aqueous catalyst system useful in olefin oxidation to a carbonyl compound which comprises:
(a) at least one molybdenum-free polyoxoanion component;
(b) at least one palladium component; and,
(c) at least one redox active metal component wherein said catalyst system is substantially free of nitrogen compounds selected from the group consisting of nitric acid, nitrogen oxides, and esters of nitrous acid.

21. The catalyst system of claim 20 wherein said redox active metal is selected from the group consisting of copper salts.

22. The catalyst system of claim 20 wherein said redox active metal is selected from the group consisting of iron salts.

23. The catalyst system of claim 20 wherein said redox active metal is selected from the group consisting of manganese salts.

24. A catalyst system useful in olefin oxidation to a carbonyl compound which comprises:
(a) at least one molybdenum-free polyoxoanion component;
(b) at least one palladium component; and,
(c) at least one nitrile ligand.

25. A catalyst system useful in olefin oxidation to carbonyl compounds which comprises:
(a) at least one molybdenum-free polyoxoanion component;
(b) at least one palladium component;
(c) at least one redox active metal component; and,
(d) at least one nitrile ligand.

26. The catalyst system of claim 25 wherein said redox active metal is selected from the group consisting of copper salts.

27. The catalyst system of claim 25 wherein said redox active metal is selected from the group consisting of iron salts.

28. The catalyst system of claim 25 wherein said redox active metal is selected from the group consisting of manganese salts.

29. An unsupported, aqueous catalyst system useful in olefin oxidation which comprises:
(a) at least one vanadium-free polyoxoanion component;
(b) at least one palladium component; and
(c) at least one redox active metal component wherein said catalyst system is substantially free of nitrogen compounds selected from the group consisting of nitric acid, nitrogen oxides and esters of nitrous acid.

30. The catalyst system of claim 29 wherein said redox active metal is selected from the group consisting of copper salts.

31. The catalyst system of claim 29 wherein said redox active metal is selected from the group consisting of iron salts.

32. The catalyst system of claim 29 wherein said redox active metal is selected from the group consisting of manganese salts.

33. A catalyst system useful in olefin oxidation which comprises:
(a) at least one vanadium-free polyoxoanion component;
(b) at least one palladium component; and
(c) at least one nitrile ligand.

34. A catalyst system useful in olefin oxidation which comprises:
(a) at least one vanadium-free polyoxoanion component;
(b) at least one palladium component;
(c) at least one redox active metal component; and,
(d) at least one nitrile ligand.

35. The catalyst system of claim 34 wherein said redox active metal is selected from the group consisting of copper salts.

36. The catalyst system of claim 34 wherein said redox active metal is selected from the group consisting of iron salts.

37. The catalyst system of claim 34 wherein said redox active metal is selected from the group consisting of manganese salts.

38. An unsupported, aqueous catalyst system useful in olefin oxidation to a carbonyl compound which comprises:
(a) at least one molybdenum-free polyoxoanion component;
(b) at least one palladium component; and,
(c) at least one redox active metal component, wherein said redox active metal is provided separate and distinct from said polyoxoanion component.

39. An unsupported, aqueous catalyst system useful in olefin oxidation which comprises:
(a) at least one vanadium-free polyoxoanion component;
(b) at least one palladium component; and
(c) at least one redox active metal component, wherein said redox active metal component is provided separate and distinct from said polyoxoanion component.

40. The catalyst system of claim 39 wherein said redox active metal is selected from the group consisting of copper salts.

41. The catalyst system of claim 39 wherein said redox active metal is selected from the group consisting of iron salts.

42. The catalyst system of claim 39 wherein said redox active metal is selected from the group consisting of manganese salts.

43. An unsupported, aqueous catalyst system useful in olefin oxidation to a carbonyl compound which comprises:
(a) at least one polyoxoanion component which is a member selected from the group consisting of compounds which have the general formula:

$$[X_xV_aM'_bM''_cO_z]^{-m}$$

wherein
X is a member selected from the group consisting of B, Si, Ge, P, As, Se, Te, I, Co, Mn and Cu;
M' and M'' are members independently selected from the group consisting of W, Mo, Nb, Ta and Re;
x is zero for isopolyoxoanions and mixed isopolyoxoanions;
x is an integer greater than zero for heteropolyoxoanions;
a, z and m are integers greater than zero;
b, c are integers; and,
$a+b+c \geq 2$;
(b) at least one palladium component; and,
(c) at least one redox active metal component provided separate and distinct from said polyoxoanion component, wherein said catalyst system is substantially free of nitrogen compounds selected from the group consisting of nitric acid, nitrogen oxides and esters of nitrous acid.

44. The catalyst system of claim 43 wherein said redox active metal is selected from the group consisting of manganese salts.

45. The catalyst system of claim 43 wherein said redox active metal is selected from the group consisting of copper salts.

46. The catalyst system of claim 43 wherein said redox active metal is selected from their group consisting of iron salts.

47. The catalyst system of claim 43 wherein said redox active metal component is a member selected from the group consisting of $CuSO_4$, $Cu(CH_3COO)_2$ and $Cu(NO_3)_2$.

48. The catalyst system of claim 43 wherein said redox active metal is selected from the group consisting of $Fe(CH_3COO)_2$, $FeSO_4$ and $MnSO_4$.

49. An unsupported, aqueous catalyst system useful in olefin oxidation to a carbonyl compound which comprises:
(a) at least one polyoxoanion component which is a member selected from the group consisting of compounds which have the general formula:

$$[X_xV_aM'_bM''_cO_z]^{-m}$$

wherein
X is a member selected from the group consisting of B, Si, Ge, P, As, Se, Te, I, Co, Mn and Cu;
M' and M'' are members independently selected from the group consisting of W, Mo, Nb, Ta and Re;
x is zero for isopolyoxoanions and mixed isopolyoxoanions;
x is an integer greater than zero for heteropolyoxoanions;
a, z and m are integers greater than zero;
b, c are integers; and,
$a+b+c \geq 2$;
(b) at least one palladium component;
(c) at least one redox active metal component provided separate and distinct from said polyoxoanion component; and,
(d) at least one nitrile ligand, wherein said catalyst system is substantially free of nitrogen compounds selected from the group consisting of nitric acid, nitrogen oxides and esters of nitrous acid.

50. The catalyst system of claim 49 wherein said redox active metal is selected from the group consisting of copper salts.

51. The catalyst system of claim 49 wherein said redox active metal is selected from the group consisting of iron salts.

52. The catalyst system of claim 49 wherein said redox active metal is selected from the group consisting of manganese salts.

53. The catalyst system of claim 49 wherein said redox active metal is selected from the group consisting of $CuSO_4$, $Cu(CH_3COO)_2$ and $Cu(NO_3)_2$.

54. The catalyst system of claim 49 wherein said redox active metal is selected from the group consisting of $Fe(CH_3COO)_2$, $FeSO_4$ and $MnSO_4$.

55. The catalyst system of claim 49 wherein said nitrile ligand is acetonitrile.

* * * * *